(12) United States Patent
Shedd et al.

(10) Patent No.: US 6,988,394 B2
(45) Date of Patent: Jan. 24, 2006

(54) APPARATUS AND METHOD OF PORTABLE AUTOMATED BIOMONITORING OF WATER QUALITY

(75) Inventors: Tommy R. Shedd, Middletown, MD (US); Mark W. Widder, Chambersburg, PA (US); Mark W. Brown, Myersville, MD (US); Murray S. Swanson, Rockyridge, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 10/774,639

(22) Filed: Feb. 3, 2004

(65) Prior Publication Data
US 2004/0206162 A1   Oct. 21, 2004

Related U.S. Application Data

(60) Provisional application No. 60/444,202, filed on Feb. 3, 2003.

(51) Int. Cl.
G01N 33/18   (2006.01)
A01K 63/00   (2006.01)

(52) U.S. Cl. .................. 73/61.41; 73/864.91; 119/224; 119/226; 340/573.1; 340/573.6

(58) Field of Classification Search .............. 73/61.41, 73/432.1, 864.91; 119/215, 224, 226; 340/573.1, 340/573.6
See application file for complete search history.

(56) References Cited

U.S. PATENT DOCUMENTS

| 3,827,283 A | * | 8/1974 | Lerner et al. .................. 73/40 |
| 4,626,992 A | | 12/1986 | Greaves et al. |
| 4,723,511 A | | 2/1988 | Solman |
| 5,140,855 A | | 8/1992 | Gruber |
| 5,307,052 A | | 4/1994 | Harrison |
| 5,469,144 A | | 11/1995 | Gradzki et al. |
| 5,804,705 A | | 9/1998 | Florion et al. .............. 73/61.41 |
| 6,058,763 A | | 5/2000 | Shedd et al. ............... 73/61.41 |
| 6,119,630 A | | 9/2000 | Lobsiger et al. |
| 6,393,899 B1 | | 5/2002 | Shedd et al. ............... 73/61.41 |

FOREIGN PATENT DOCUMENTS

| GB | 2195 543 A | 4/1988 |
| WO | WO 95/14925 A1 | 6/1995 |
| WO | WO 98/41862 | 9/1998 |

OTHER PUBLICATIONS

ASTM Standard Guide for Ventilatory Behavorial Toxicalogy Testing of Freshwater Fish, E1768-95,9,ASTM, West Conshohocker, PA.

(Continued)

*Primary Examiner*—Daniel S. Larkin
(74) *Attorney, Agent, or Firm*—Elizabeth Arwine

(57) ABSTRACT

A portable automated biomonitoring system for monitoring water quality includes an exposure chamber for housing an aquatic organism and a water inlet for directing water to the exposure chamber. The aquatic organism has ventilatory behavior and body movement sensitive to water quality. Electrodes sense electrical signals produced by the organism during its ventilatory behavior and body movement, and a controller responsive to signals from the electrodes determines a plurality of ventilatory parameters based on the signals. The ventilatory parameters are compared with corresponding thresholds to determine when the water to which the organism is exposed has caused physiological stress to the organism. The water being evaluated may be recirculated through the system for further analysis.

19 Claims, 15 Drawing Sheets

OTHER PUBLICATIONS

Carlson, R. W. et al., "Fish Cough Response—A Method for Evaluating Quality of Treated Complex Efffluents", Water Research, 1978, vol. 12, pp. 1-6.

"Real-Time Monitoring for Toxicity Caused by Harmful Algal Blooms and Other Water Perturbations", EPA Nov. 2001.

Continous Automated Biomonitoring: Perspectives and Applications, U.S. Army Corps of Engineers Seventh Innovative Technology Transfer Workshop, Mar. 20, 1997.

Gruder, D. et al., "Initial Testing of a recent Biological Monitoring Concept", Journal of Water Pollution Control Federation, Nov. 1979, vol. 51, No. 11, pp. 2744-2751.

Nelms, et al. "BeRM: Bioelectric Response Monitor", proceedings from IEEE SouthEast Con 92, Apr. 12-15, 1992, Birmingham, Alabama, IEEE, vol. 1, No. 12, pp. 91-94.

Shedd, Tommy R. et al., "Evaluation of an Automated Fish Ventilatory Monitoring System in a Short-Term Screening Test for Chronic Toxicity," U.S. Army Biomedical Research and Development Laboratory, Technical Report AD A172116, Fort Detrick, MD, Jul. 1986.

Shedd, Tommy R., et al., "Long-Term Opeation of an Automated Fish Biomonitoring System for Continuous Effluent Acute Toxicity Surveillance", Bull. Environ. Contam. Toxicol, 2001, pp. 392-399.

Van Der Shalie, W. H., "A New Technique for Automatic Monitoring of Fish Ventilatory Patterns and Its Possible Use in Screening Tests for Chronic Toxicity" In Aquantic Toxicology; Third Conference ASTM STP 707; J. Eaton, P. Parrish, and A. Hendricks (eds.), Philadelphia, PA. 1980, pp. 233-242.

Van Der Shalie, W. H. et al., "Ventilatory and Movement Response of Rainbow Trout Exposed to 1,3,5-Trinitrobenzene in an automated Biomoniting System", Automated Biomonitoring—Living Sensors as Environmental Monitors (eds.), Ellis Horwood Publishers, West Sussex, England, 1988, pp. 67-74.

Westlake, G. F. et al., "Evaluation of An Automated Biological Monitoring System at an Industrial Site", In ASTM STP 607, J. Cairns, Jr., K.L. Dickson, and G.F. Westlake, (eds.), 1997, pp. 30-37.

* cited by examiner

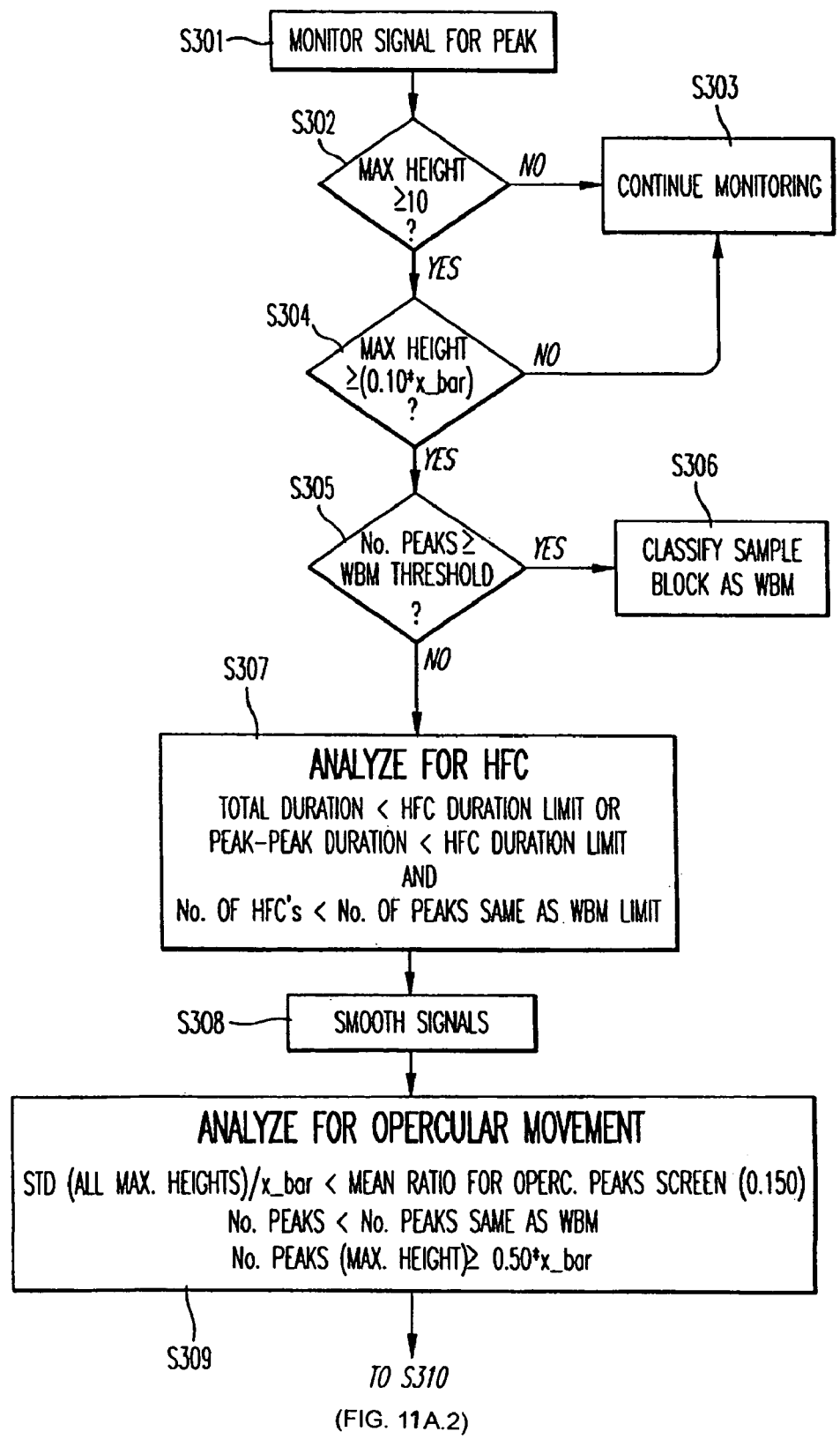
FIGURE 11A.1

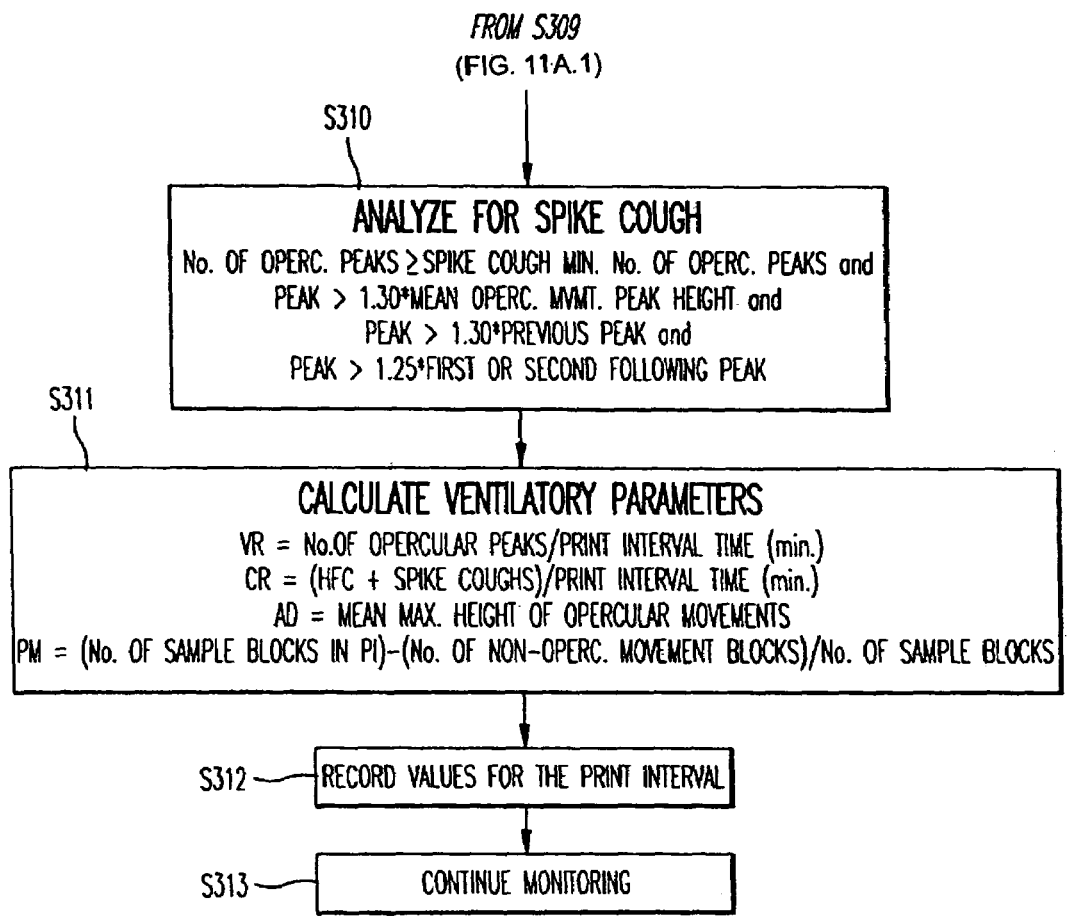
FIGURE 11A.2

APPARATUS AND METHOD OF PORTABLE AUTOMATED BIOMONITORING OF WATER QUALITY

This application claims the benefit of U.S. Provisional Application Ser. No. 60/444,202, filed Feb. 3, 2003, which is hereby incorporated by reference.

I. FIELD OF THE INVENTION

The present invention relates generally to an apparatus and method for monitoring water quality. More particularly, the present invention relates to a portable apparatus and method for monitoring water quality using the ventilatory behavior and body movement of aquatic organisms.

II. BACKGROUND OF THE INVENTION

Ventilatory responses are often some of the first prelethal symptoms exhibited by animals to environmental stressors. Continued, abnormal ventilatory behavior, such as rapid, shallow, or erratic breathing, can indicate physiological damage that may be irreversible. Changes in the ventilatory behavior of fish have been shown to be a reliable indicator of accidental toxic spills or "slugs" of pollutants in wastewater and drinking water systems. Accordingly, ventilatory biomonitoring systems can serve as an early indicator of impending damage to aquatic ecosystems and possible harm to humans.

The technological means are readily available to log and display ventilatory signals for subsequent analysis. As a result, there are a considerable number of studies that have examined ventilatory behavior of fish and other aquatic organisms. A large number of substances at lethal levels have been shown to elicit ventilatory responses relatively quickly. For many pollutants, a significant response was often generated in less than one hour of exposure to concentrations approaching the 96-hour LC50 (the concentration at which fifty percent of the organisms expire within 96 hours of exposure). Studies performed using subacutely toxic samples of effluents or individual pollutants (concentrations well below the reported LC50 concentration) often documented responses within one to ten hours of exposure.

Although a variety of organisms have been examined for this purpose, including crayfish, aquatic insect larvae, and bivalves, most research in aquatic ventilatory behavior has used freshwater fish species. This is largely because fish are generally more ecologically "visible" in their importance in aquatic systems and many species (particularly the salmonids and centrarchids) have large opercular flaps that yield relatively clear ventilatory signals for measurement and evaluation.

The ventilatory parameters in fish that have been shown to be affected by toxicity include ventilatory rate (opercular movement over time), depth of ventilation (amplitude), coughing or gill purge rate, and erratic episode frequency due to sudden movement of the organism. Most commonly, changes in just ventilatory rate, as opposed to the other parameters just mentioned, have been used as a bioindicator of toxic conditions. The depth of ventilation and gill purge or cough rate, however, have been reported to be more sensitive indicators of toxicity for some compounds.

Changes in ventilatory rate are often determined by manual examination of the peaks per unit area on a strip-chart recording. Depth of ventilation or signal amplitude is similarly measured from top to bottom of the waveform on the strip chart. Cough rate has been more difficult to determine even with manual examination of a strip chart as several different types of coughs may be present, with their own corresponding characteristic waveform pattern. Also, without the use of simultaneous video techniques, the actual occurrence of a cough is not always clear.

Another important aspect of water quality analysis is the ability to test water from a variety of sources at different locations. This is especially important when the water draining into a body of water comes from different sources. However, the nature and size of water monitoring equipment typically prevents such field testing.

III. SUMMARY OF THE INVENTION

Accordingly, one object of the present invention is to provide a portable apparatus for automated biomonitoring of water quality.

Another object of the present invention is to be able to include behavioral parameters such as the depth of ventilation, cough rate, and whole body movement of an aquatic organism in addition to ventilatory frequency data in the portable automated biomonitoring of water quality.

A related object of the present invention is to be able to further include water quality characteristics such as dissolved oxygen, pH, temperature, and conductivity in the portable biomonitoring of water quality.

Another object of the present invention is to provide improved waveform processing of data signals from aquatic organisms to reduce spurious data signals.

Another object of the present invention is to provide a portable array of biomonitor exposure chambers with an integral water delivery and drain system for improved ventilatory signal data collection and biomonitoring operation.

Another object of the present invention is to provide a programmable alarm response that includes automated water sampling and optional remedial action such as isolation of a water pollution source.

Many of these objects are met by a portable system for monitoring and evaluating water quality including an exposure chamber for housing an aquatic organism and configured to contain water to be monitored, a water inlet for directing water to the exposure chamber, and electrodes for sensing electrical signals generated by the organism during ventilatory behavior and body movement in the water being monitored. The electrodes quantify the generated electrical signals into data and output the data as a behavioral signal. Electrical signals picked up and quantified by the electrodes may be supplied to an automatic controller, which determines a plurality of ventilatory and body movement parameters based on the signals from the electrodes. The controller compares the parameters with corresponding thresholds to determine when the water to which the organism is exposed has caused physiological stress to the organism. A recirculating apparatus recirculates water to the exposure chamber for further testing.

The system provides electrical signals to the controller or similar device for determining a wide variety of ventilatory and body movement parameters. In a preferred embodiment, the apparatus provides electrical signals for determining at least the ventilatory frequency, the average ventilatory depth, and the cough rate of the organism.

The system may further include various devices operative in response to a determination of a water quality problem by the controller. For example, it may include an alarm mechanism, which generates an alarm, a sample device which collects samples of the water being monitored for subsequent analysis, or a diverting mechanism for diverting the water being monitored to a storage tank and preventing the water form being discharged into the environment. Furthermore, the water being monitored can be temperature controlled through the use of a heater/chiller unit.

The recirculating apparatus may include a water reservoir, a water quality sensor and a water pump for pumping water from the water reservoir to the water quality sensor and into the exposure chamber. The recirculating apparatus is particularly advantageous as it helps to ensure test organism safety. The water quality sensor may detect a characteristic of the water supplied to the exposure chamber. The controller is responsive to the water quality sensor by comparing the water characteristic with the corresponding behavioral signal to determine when a change in one or more of the ventilatory parameters occurred at the approximate time that a change in water characteristic occurred.

Another aspect of the present invention relates to a method of evaluating water quality including the steps of delivering water to be evaluated to a water reservoir and pumping the water from the water reservoir to an exposure chamber housing at least one aquatic organism. Electrical signals generated by the aquatic organism are measured, and a plurality of ventilatory parameters of the aquatic organism are determined based on the electrical signals. The water in the exposure chamber is then drained back into the reservoir. The water is then pumped from the reservoir back into the exposure chamber for further analysis. Alternatively, the water in the reservoir is pumped from the reservoir through a source water outlet where it exits the system.

The method may further include pumping the water from the water reservoir through a water quality sensor wherein the water quality sensor detects a characteristic of the water before it is supplied to the exposure chamber. In addition, the method may include maintaining the temperature of the water being evaluated within the exposure chamber at a predetermined value.

The monitoring and determination of ventilatory and body movement parameters of an aquatic organism by a portable automated system as taught in the present invention provides for continuous, around-the-clock monitoring of water quality with fast signal processing and good reproducibility of results, which are otherwise not possible with manual methods of biomonitoring. The present invention uses a plurality of ventilatory and body movement parameters to provide greater detection sensitivity and accuracy over systems using a one-parameter analysis, and the present invention is readily integrated with effluent control systems for wastewater treatment plants, factories, and other possible sources of pollutants. The present invention also may be used to monitor and evaluate the quality of a body of water such as a lake or stream, or the inlet to a potable water treatment facility, providing a detection capability of inadvertent or intentional toxic contamination of the water source. Such contamination could otherwise go undetected without the present invention until human health is affected and traced to the source of contaminated drinking water. In addition, the exposure chamber of the present invention provides improved biomonitoring of aquatic organisms with a top-bottom electrode arrangement, uniform mixing of the water prior to organism exposure, and reduced water stratification within the chamber. Because the method of the present invention is easily transportable, it may be quickly implemented in a variety of environments unlike existing biomonitoring methods.

In the following description, reference is made to the accompanying drawings, and which are shown by way of illustration to the specific embodiments in which the invention may be practiced. The following illustrated embodiments are described in sufficient detail to enable those skilled in the art to practice the invention. It is to be understood that other embodiments may be utilized and that structural changes based on presently known methodology and/or functional equivalents may be made without departing from the scope of the invention.

Given the following detailed description, it should become apparent to the person having ordinary skill in the art that the invention herein provides a novel apparatus and method for portable and automated biomonitoring of water quality.

IV. BRIEF DESCRIPTION OF THE DRAWINGS

Figure 11B:
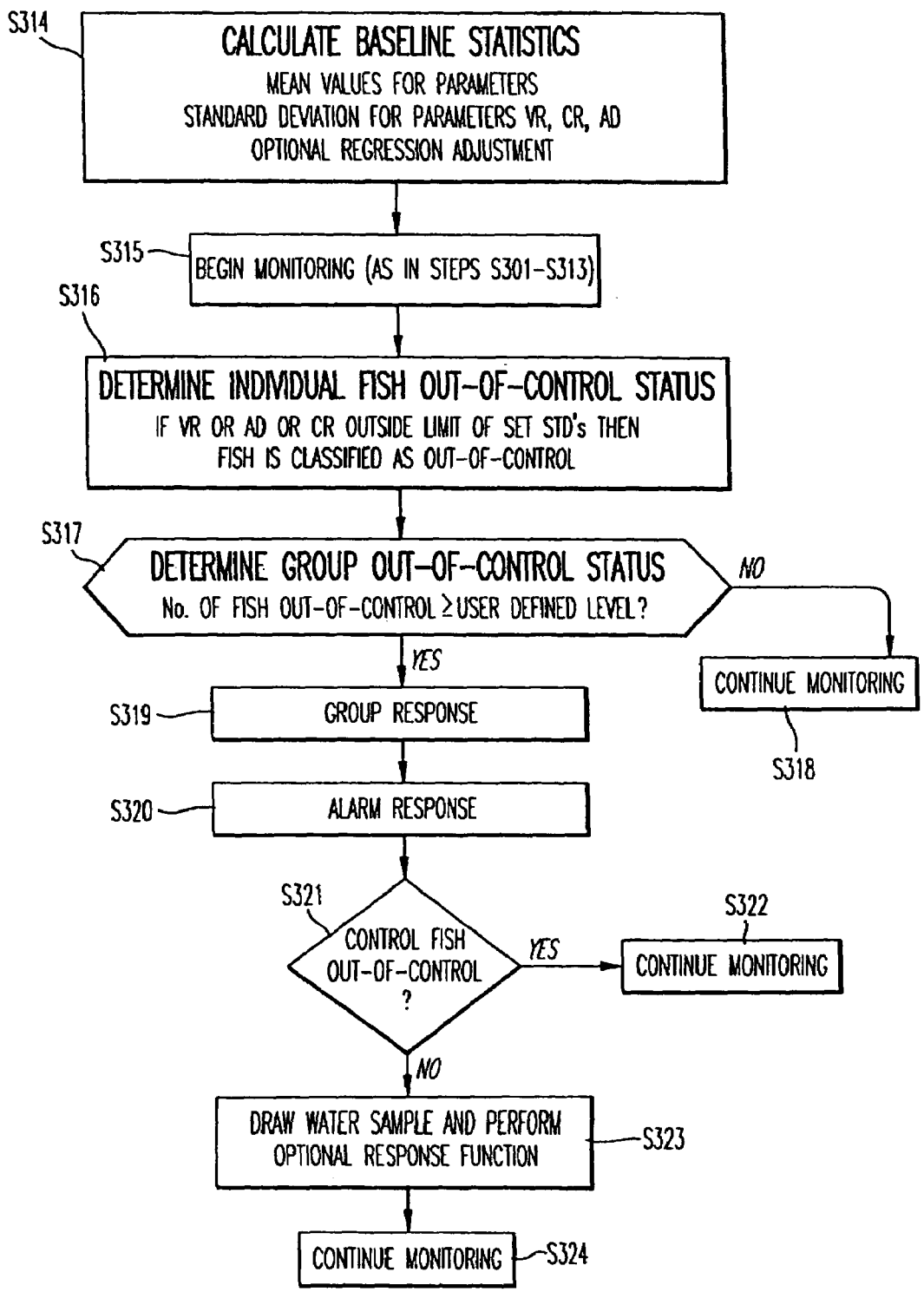

FIGS. 11A–11B display a flowchart illustrating a process for distinguishing between coughs, whole body movement, changes in ventilatory rate, and other behavior to determine when en alarm state occurs in the present invention.

Figure 12:
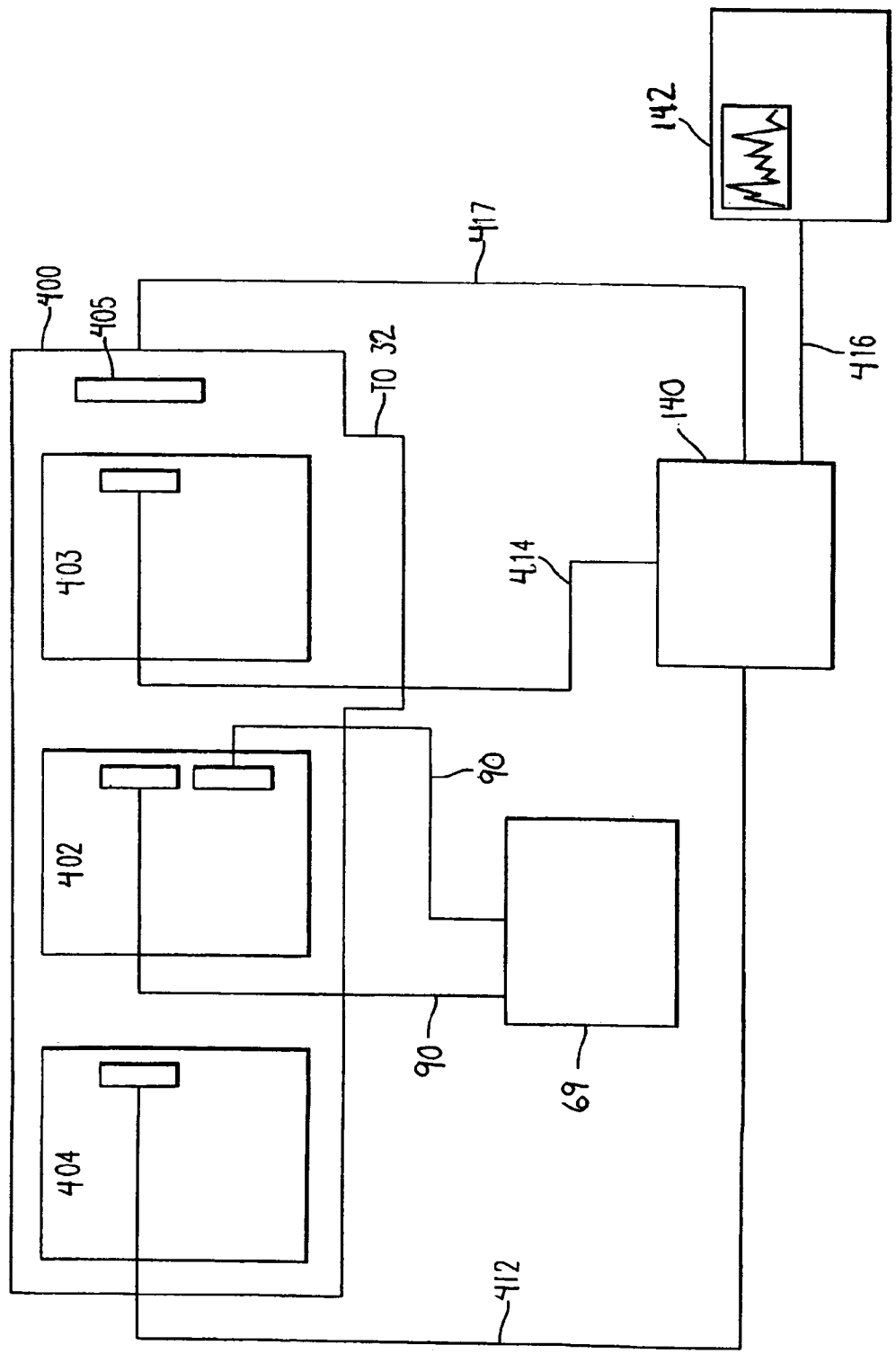

FIG. 12 is a schematic of an internal carrier board which can be used in the present invention for integration with a standard microprocessor.

Figure 13:
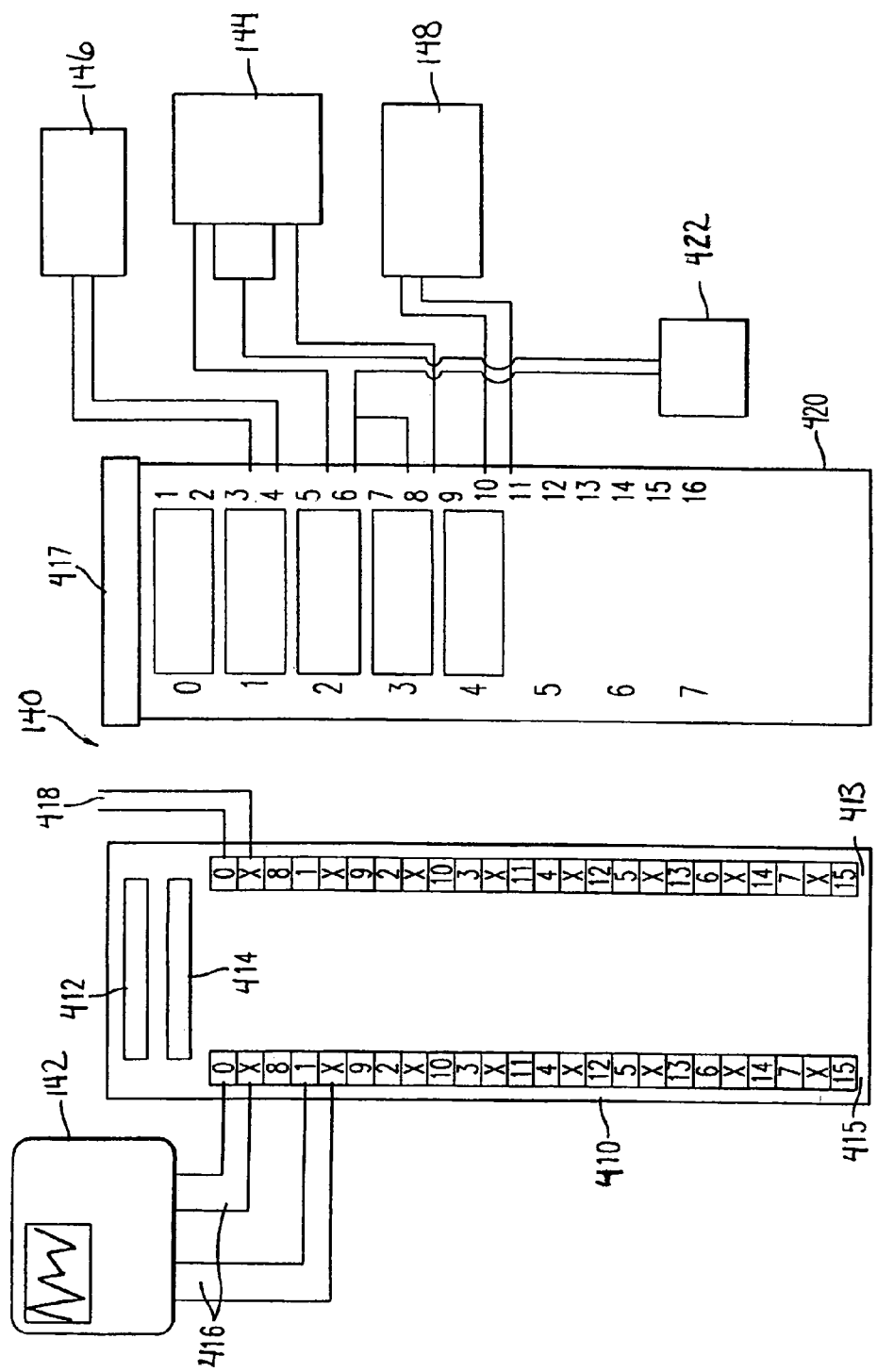

FIG. 13 is a schematic of a termination panel used as an interface between a microprocessor and other components of the present invention.

V. DETAILED DESCRIPTION

Figure 1:
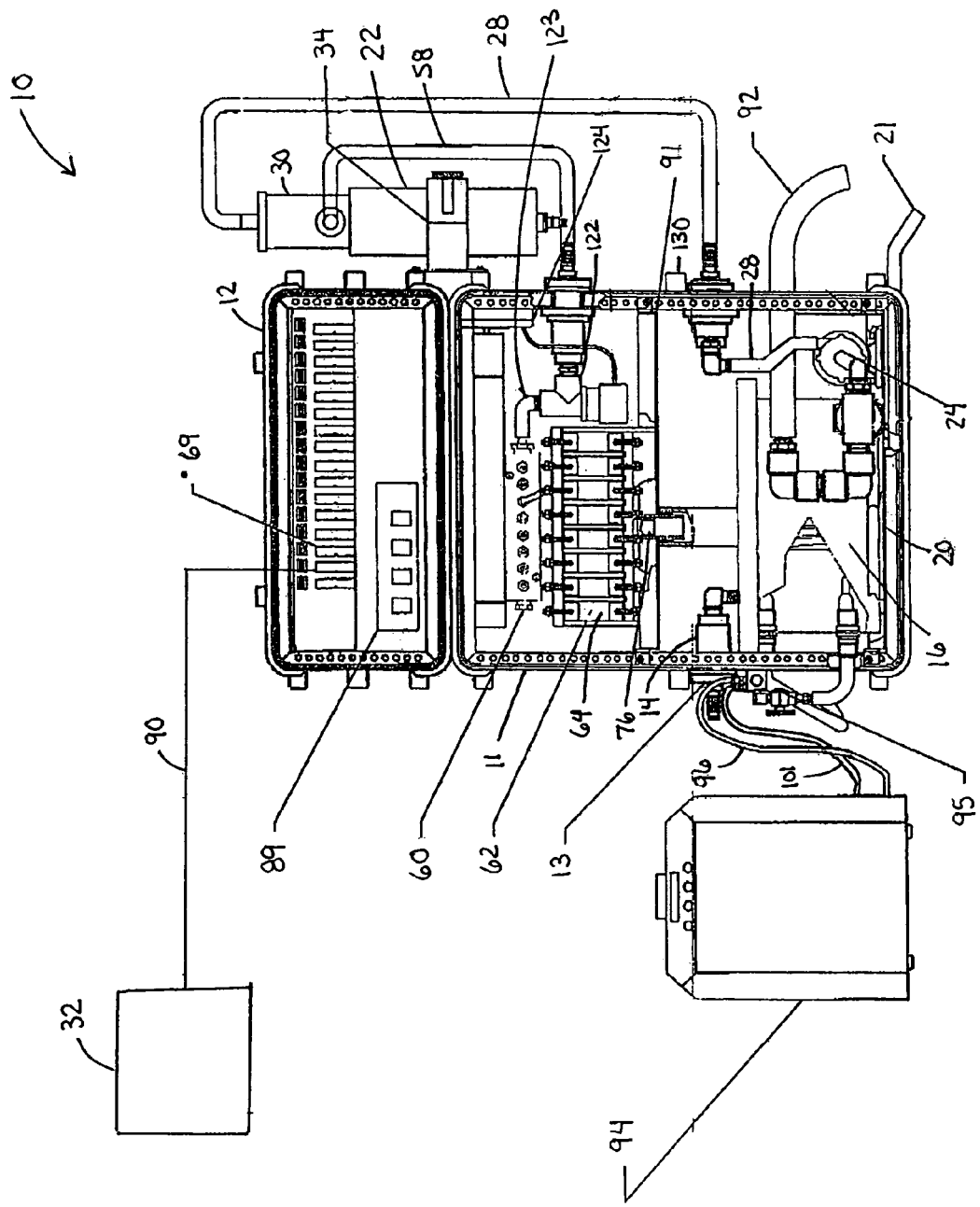
FIG. 1 is a cross sectional view of an embodiment of a portable automated biomonitoring system according to the present invention.

FIG. 1 illustrates a cross-sectional view of an embodiment of a portable automated biomonitoring system 10 in accordance with the present invention. The system 10 preferably includes a first portable housing 11 and a second portable housing 12 in communication with and located on top of the first housing. The first and second housings 11 and 12, are preferably rectangular in shape; however, the housings may be any shape which allows for proper operation of the system 10. The housings 11 and 12 may be comprised of a variety of materials including any material having sufficient weight, corrosion resistance and the ability to protect the monitoring components of the system 10 located within the housings. Examples of suitable materials include, but are not limited to plastic, fiberglass, aluminum or titanium. Preferably, the housings 11 and 12 are comprised of reinforced molded plastic. For example, the first housing 11 may be an SKB 21" Black Rack Box and the second housing may an SKB 7" Black Rack Box, both from Specialized Products, Southlake, Tex. Typically, the first housing 11 contains the water and aquatic organisms being analyzed, and the second housing 12 contains the electrical components in the system 10, as shown in FIG. 1.

Unless indicated otherwise, it should be understood that the preferred embodiment of the biomonitoring system 10 includes two identical halves (only one being shown in FIG. 1), wherein each half comprises the same components which will be described in more detail below. The system 10 includes at least one source water inlet 13 through which water flows from a source (not shown) and into the portable monitoring system. The source water to be monitored and analyzed by the present invention may be from any source of water. Water to be monitored includes, but is not limited to, naturally occurring water sources such as lakes, rivers, streams, and harbors, and other natural bodies of water. The water source to be monitored may also come from a source of drinking water as it is supplied to the inlet of a potable water treatment facility, or may be taken from a possible pollution source such as the discharged water from a facility for treating wastewater or groundwater before the water is discharged from the treatment facility. The source water may be supplied to the source water inlet 13 by any method known to those having skill in the art including, but not limited to the use of a pump, pressure, gravity, etc.

Figure 7C:
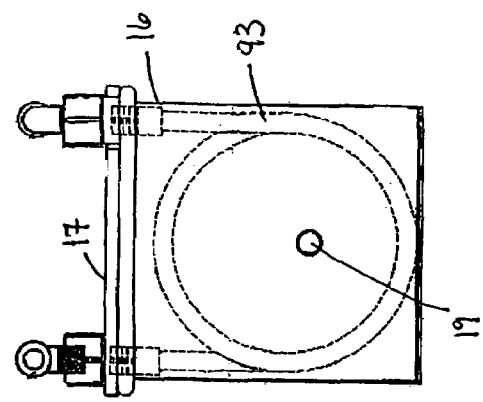
FIGS. 7B–7C are side views of a reservoir.
Figure 7A:
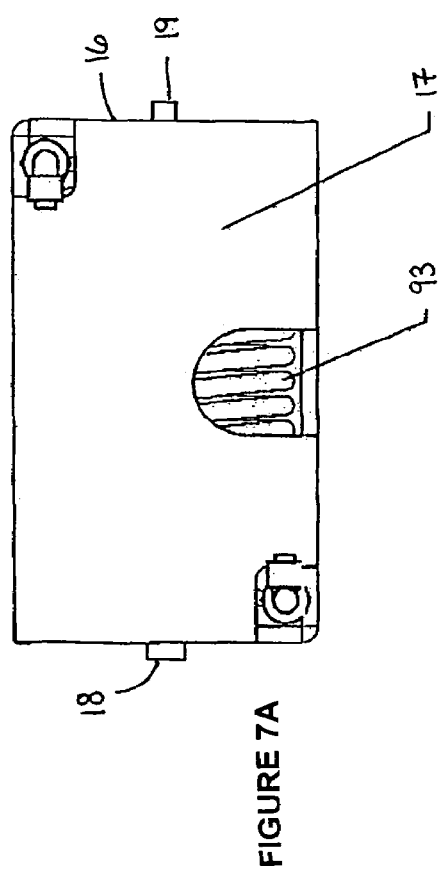
FIG. 7A is a top view of a reservoir of a biomonitoring system made in accordance with the present invention.
Figure 7B:
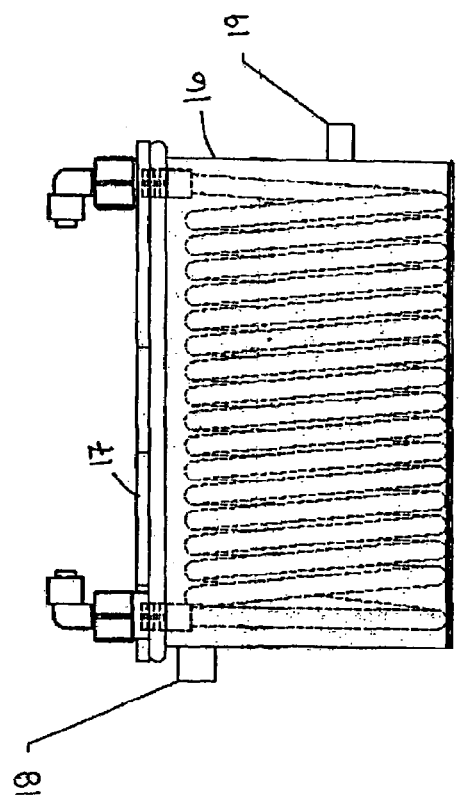

The water to be analyzed flows through the water source inlet 13 and then passes through an inlet conduit 14 and into a water reservoir 16, which is preferably disposed within first housing 11. As shown in FIG. 7, the reservoir 16 includes a lid 17, a reservoir inlet 18 through which the source water enters, and a reservoir outlet 19. A reservoir overflow pan 20 catches water which may be leaking from pipes or from other areas within the entire system 10 and directs the water outside of the system via an overflow drain 21 which preferably includes a conduit extending outside of housing 11. The water is contained in the water reservoir 16 prior to being tested. The reservoir 16 volume may vary depending upon the dimensions of the housing 11. The water reservoir 16 preferably has a volume between about one and about four gallons. Preferably, the water reservoir 16 has a volume between about one and about two gallons.

The water may then be pumped out of the water reservoir 16 through outlet 19 to a water quality sensor 22 via a pump 24. The water quality sensor is preferably located outside of the housings 11 and 12. Specifically, the water may be pumped from the reservoir 16 through a sensor inlet conduit 28 and into a water quality cup 30. Any pump known to those having skill in the art may be used in the present invention. The water contained in the water quality cup 30 is analyzed by the water quality sensor 22. The water quality sensor 22 monitors and analyzes various parameters of the water including, but not limited to dissolved oxygen level, temperature, pH, and conductivity. Through the use of a controller 32 these parameters may be monitored and compared to present alarm limits.

Figure 2:
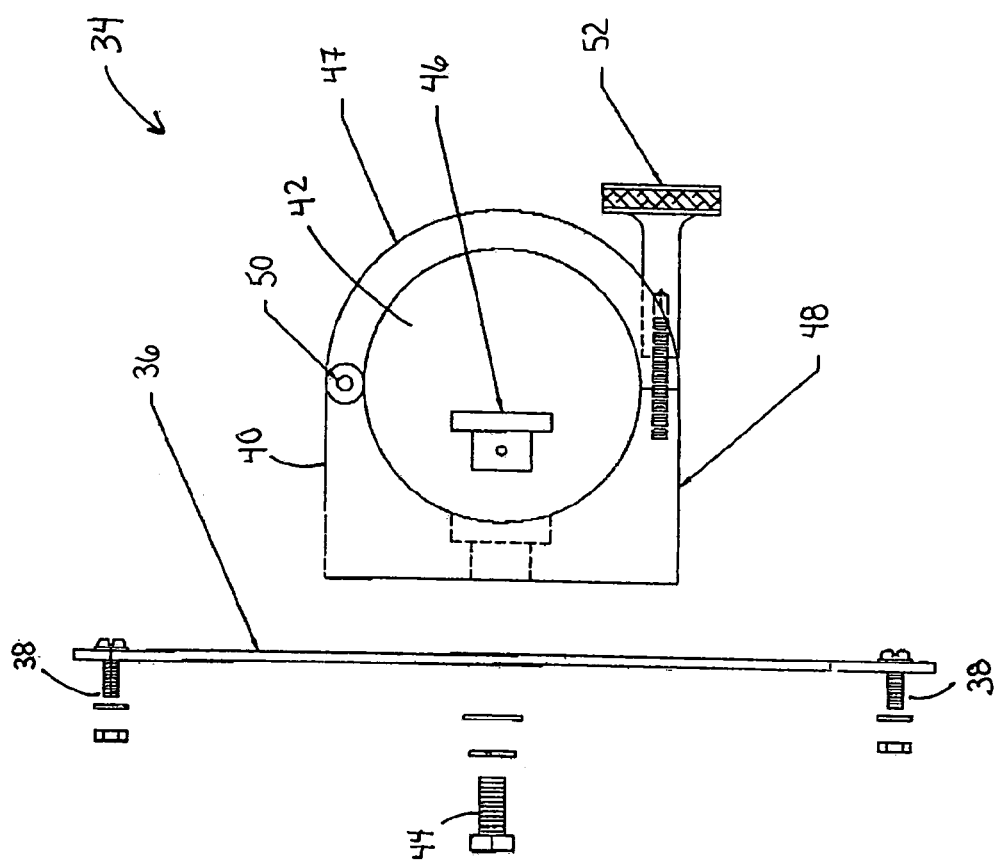
FIG. 2 is a top view of a calibration bracket of a biomonitoring system made in accordance with the present invention.

Preferably, the water quality sensor 22 is pivotally attached to the exterior of the first and second housings 11 and 12 via a calibration bracket 34 which is shown in more detail in FIG. 2. The calibration bracket 34 comprises a plate 36 which is mounted to the exterior of housings 11 and 12. The plate 36 is preferably mounted via screws 38. A clamp 40 having an orifice 42 therein is pivotally mounted to the plate via a pivot screw 44 and pivot 46. The pivot screw 44 engages the pivot 46 allowing for pivotal movement of the clamp 40. The clamp 40 may comprise a top half 47 and a bottom half 48 wherein each half is connected together via a dowel pin 50. The calibration bracket 34 further comprises a knob 52 for opening and closing the clamp 40 in order to place the water quality sensor 22 inside of the clamp.

The pivotal movement of the water quality sensor 22 allows for flow-through operation and calibration of the system 10 without the laborious task of disconnecting and remounting the sensor. The pivotal rotation of the water quality sensor 22 also enables one individual to perform maintenance of the sensor without an additional clamp setup or additional individual to hold it. Pivotal movement of calibration bracket 34 allows for positioning of the sensor 22 in a manner that does not trap air within the sensor which would prevent proper water monitoring.

Figure 3B:
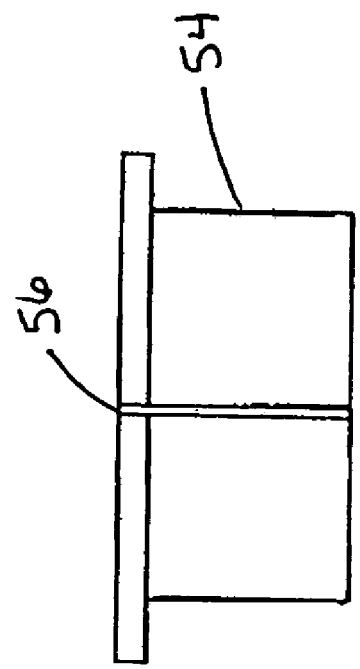
FIG. 3B is a side view of a water analyzer conversion sleeve.
Figure 3A:
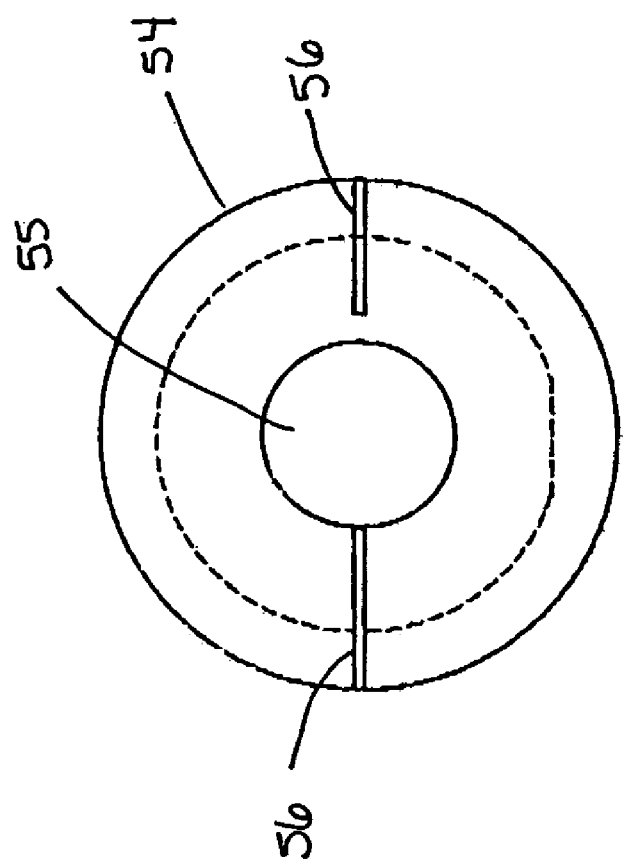
FIG. 3A is a top view of a water analyzer conversion sleeve of a biomonitoring system made in accordance with an embodiment of the present invention.

Referring to FIGS. 3A–3B, a water analyzer conversion sleeve 54 may be utilized to adapt the calibration bracket 34 to fit different models of water quality sensors 22. The water analyzer conversion sleeve 54 is preferably cylindrical in shape and comprises an orifice 55 inside which a water quality sensor 22 fits. The conversion sleeve 54 includes at least one slot 56 which allows the sleeve to be partially opened and closed. The water analyzer conversion sleeve 54 may be placed inside of the calibration bracket 34, thereby allowing water quality sensors 22 having smaller diameters to fit inside of the calibration bracket. The slots 56 located in the conversion sleeve 54 allow the sleeve to be partially opened during the placement of a water quality sensor 22 within the sleeve. When the clamp 40 on the calibration bracket 34 is closed and tightened, the slots 56 located in the conversion sleeve 54 are also closed.

Figure 4:
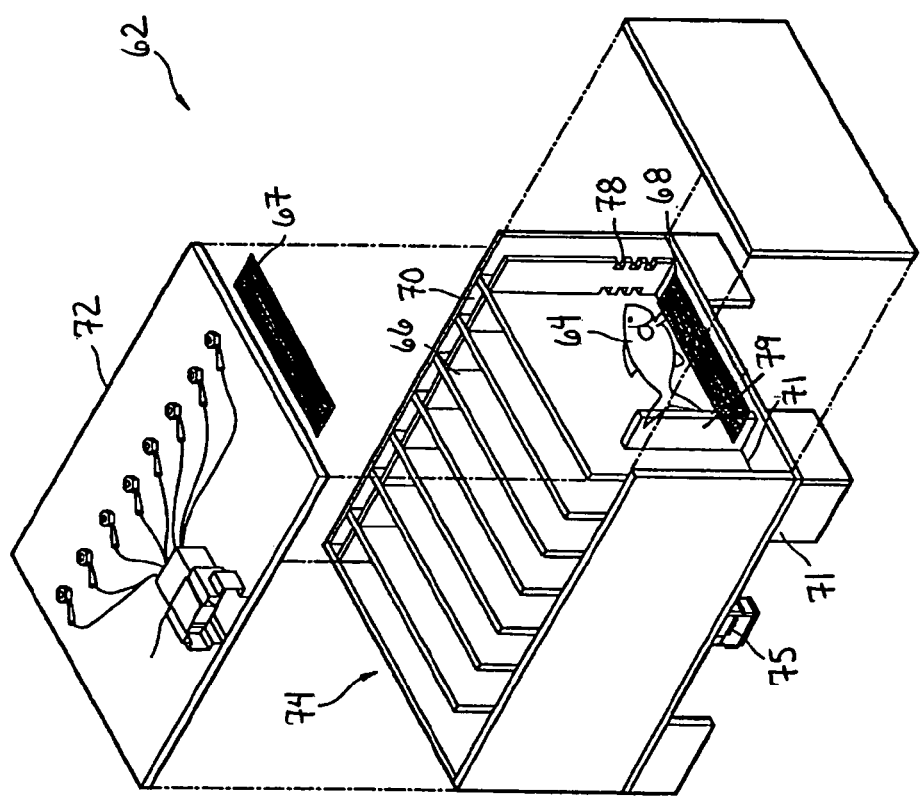
FIG. 4 is a perspective view of an exposure chamber of a biomonitoring system made in accordance with the present invention.

Returning to FIG. 1, once the water is analyzed by the water quality sensor 22, it exits the sensor via a sensor outlet conduit 58 which is connected to a water distribution manifold 60. The water passes through the water distribution manifold 60 and into an exposure chamber 62 containing one or more aquatic organisms 64, such as fish. The exposure chamber 62 may include one or more chamber compartments 66 for holding an individual fish 64 as shown in FIG. 4, wherein the water distribution manifold 60 distributes water into each chamber compartment. For example, in a preferred embodiment, the exposure chamber 62 includes eight chamber compartments 66, and the water distribution manifold 60 distributes water into each chamber compartment. Eight fish 64 exposed to the same water provide a statistically significant sample group of organisms to determine whether physiological stress has occurred due to the water quality as opposed to illness in, or injury to, an individual fish that was caused by something other than water quality. For example, in the preferred embodiment, the system 10 includes a total of two exposure chambers 62 wherein each exposure chamber includes eight chamber compartments 66. Accordingly, one group of fish 64 may be exposed to a water sampling source and the other group of fish may be exposed to control water. Alternatively, one group of fish 64 may be monitored while another group is being acclimated or monitored for benchmark data prior to exposure. Furthermore, if two portable systems 10 of the present invention are utilized, a total of four exposure chambers 62, each having eight chamber compartments 66 allow for simultaneous monitoring of up to thirty-two fish.

Turning to FIG. 4, a perspective view of an exposure chamber 62 for housing fish or other aquatic organisms 64 is illustrated. Exposure chamber 62 provides a compact and convenient array of eight individual chamber compartments 66, each with top electrode 67, bottom electrode 68, water input pre-chamber 70, and drain post-chamber 71. The electrodes 67 and 68 capture physiological signals of a fish 64 and transmit the signals to an amplifier 69 (shown in FIG. 1) where the electrical signals are filtered and amplified. Electrodes 67 and 68 and wiring connections are preferably made from a corrosion resistant material. Exposure chamber top 72 includes waterproof electrical plug 73, which is connected to each of the top electrodes 67. When placed on top of base 74, top 72 covers exposure chambers 66 and drain post-chamber 71 leaving water input pre-chambers 70 open to receive a water inlet supply from the water distribution manifold 60. The walls of the chamber compartments 66 preferably reduce or prevent visual contact between adjoining compartments. For example, the walls may be frosted or opaque plastic as opposed to the clear plastic used for the remainder of base 74 and top 72. This helps to reduce fish stimuli that would otherwise occur with visual contact between fish in adjacent compartments. Clear plastic is preferred for the top and bottom to allow the chamber contents to be viewed from above or below.

The electrodes 67 and 68 may be made of a wide variety of materials. One example of a readily available, corrosion resistant material which can be used is stainless steel. However, in some situations, metal electrodes may undergo galvanic interactions with water in the exposure chambers 66, particularly when the water has a high conductivity on the order of 4720 $\mu$S/cm or above (occurring, for example, with a salinity level of approximately 3 ppt), resulting in increased noise and signal instability. In such situations, it may be preferable to employ a nonmetallic material, such as graphite, for the electrodes 67 and 68.

Figure 5A:
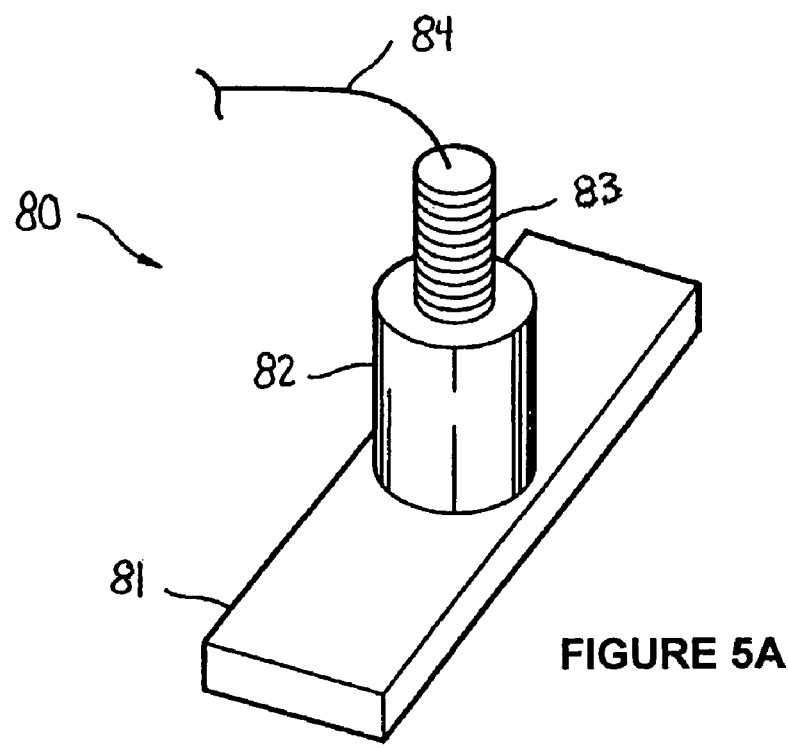
FIG. 5A is a perspective view of an electrode assembly of a biomonitoring system made in accordance with the present invention.
Figure 5B:
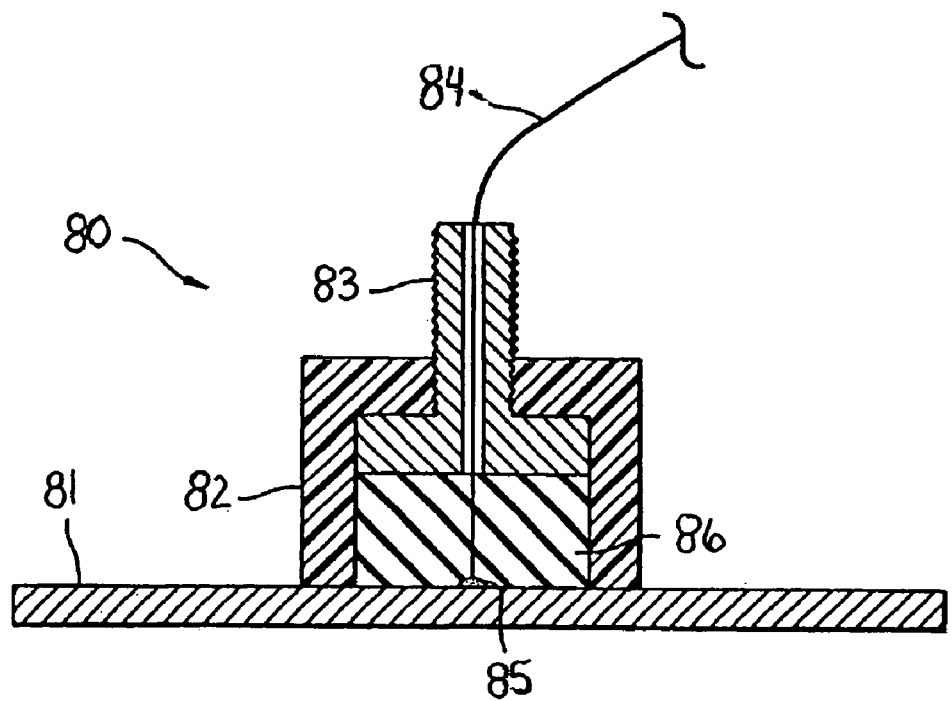
FIG. 5B is a vertical cross-sectional view of an electrode assembly of a biomonitoring system made in accordance with the present invention.

FIGS. 5A and 5B are respectively a top perspective view and a vertical cross-sectional view of an example of an electrode assembly 80 which can be used as one or both electrodes 67 and 68. The illustrated assembly 80 includes an electrically conducting electrode plate 81, a spacer 82 for positioning the plate 81 with respect to the interior of an exposure chamber 62, and a bolt 83 for securing the assembly 80 to the exposure chamber 62. The illustrated plate 81 is an elongated rectangular strip of graphite with a width of 0.8 inches and a length of 3.5 inches, although the dimensions of the plate 81 are not critical. The spacer 82, which is made of acrylic or other electrically insulating material, is secured to the plate 81 by any convenient manner, such as by bonding. It has a central bore for receiving the bolt 83, which in this example is made of nylon or other electrically insulating material. The bolt 83 has a central bore through which can pass a lead wire 84 which is electrically connected to the plate 81 in any manner which assures good electrical conductivity, such as by using a conductive bonding material 85 of silver epoxy or other suitable material.

The interior of the spacer 82 between the head of the bolt 83 and the plate 61 may be filled with a nonconductive epoxy 86 or other nonconductive material in order to make the interior of the spacer 82 water tight and to increase the structural stability of the connection between the lead wire 84 and the plate 81. The threads of the bolt 83 which extend outside of the spacer 82 may be passed through a corresponding opening in the exposure chamber 62 and affixed with a nut on the exterior of the exposure chamber 62 to secure the electrode assembly 80 in place. Each spacer 82 is sufficiently long that at least one face of the corresponding plate is immersed in the water in the exposure chamber 62. The lead wire 84 can be connected to the plug 73 so that the output signals from the assembly 80 can be supplied to the amplifier 69 or to external equipment if desired.

Figure 6:
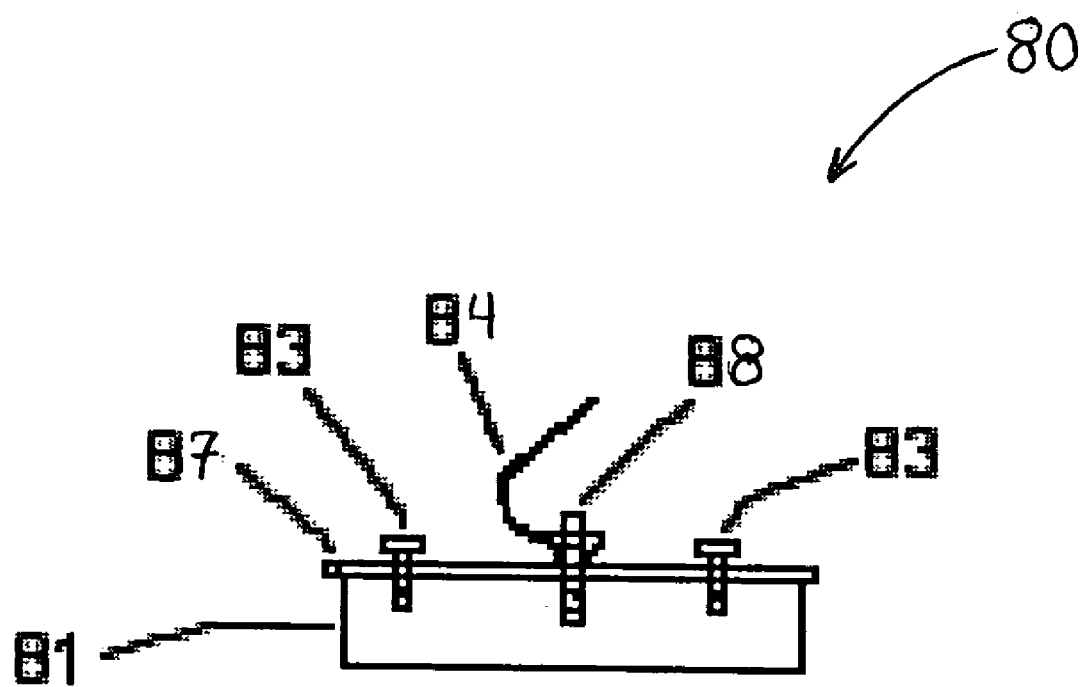
FIG. 6 is a cross-sectional view of an electrode assembly of a biomonitoring system made in accordance with an alternative embodiment of the present invention.

FIG. 6 illustrates a preferred embodiment of an electrode assembly 80 which can be used in the present invention. The electrode assembly 80 can be used as one or both electrodes 67 and 68. In this embodiment, the electrode assembly 80 includes an electrically conducting electrode plate 81, a non-conductive gasket 87 for sealing the electrode to the top or the bottom of the exposure chamber 62, and two non-conducting bolts 83 for securing the electrode assembly 80 to the exposure chamber. The center bolt 88 is comprised of an electrically conductive material, and is threaded tightly into the plate 81 in a manner which assures good electrical conductivity. The two bolts 83 may be tightened to secure the electrode plate 81 to the exposure chamber 62 forming a water tight seal as the electrode compresses the gasket 87. The wire 84 can be secured to the conductive bolt 88 with a nut. The wire 84 can be connected to the plug 73 so that the output signals from the assembly 80 can be supplied to the amplifier 69 or to external equipment if desired.

Returning to FIG. 4, base 74 includes a waterproof electrical plug 75, which is electrically connected to each of the bottom electrodes 68. Base 74 further includes a drain 76 (see FIG. 1), and may also include legs 77. When in use with the present invention, water flows into the exposure chamber 62 through the water inlet chambers 70 where it enters the chamber compartments 66 through holes 78. Water flows out of the chamber compartments 66 by flowing over overflow dividers 79 and into a drain chamber 71. This flow path from low inlet to high outlet provides increased water mixing and reduced stratification within the chamber compartments 66 to ensure that all the fish 64 are exposed to the same water conditions and water quality. After leaving the chamber compartment 66, water flows into drain post-chamber 71 which serves as a common reservoir for drain water from all eight chamber compartments 66. Water flows out of the post-chamber 71 via drain 76, and back into the reservoir 16.

In addition to providing inlet water mixing and reduced stratification within the chamber compartments 66, the exposure chamber 62 provides a compact and convenient array of eight chamber compartments that can be installed, removed, and inspected with minimal effort. The top-bottom electrode arrangement of the exposure chamber 62 provides for improved detection of ventilatory responses as compared to a front-back arrangement. Normally a fish 64 in such a tank will orientate its head upstream towards the front panel of the tank, but will occasionally change its position and orientation in the tank. A front-back electrode arrangement can cause signal alteration due to changes in fish position and orientation relative to the electrodes, but a top-bottom arrangement is much less affected by such changes.

While a preferred embodiment of an exposure chamber 62 has been described and illustrated, various modifications and variations are possible. For example, the number of chamber compartments 66 per exposure chamber 62 could vary and the pre-chamber 70 and post-chamber 71 could be modified while still providing uniform mixing of the water prior to organism exposure, and reduced water stratification within the chamber as taught above.

The signals picked up by the electrodes 67 and 68, which will be referred to as ventilatory signals, are in analog form. The terms "ventilatory signal" and "ventilatory parameter" as used herein include data representative of body movement other than the movement of opercular flaps. Such non-opercular movement could, for example, include data resulting from an erratic episode due to sudden movement of the aquatic organism 64 within the exposure chamber 62. The analog ventilatory signals picked up by electrodes 67 and 68 are provided by amplifier 69 to a controller 32 via signal cables 90. As fully described below, a controller 32 or similar device is used to convert the analog electrical signals to digital signals, to further amplify and filter the signals, and to perform an analysis to determine ventilatory and body movement parameters, such as ventilatory rate, cough rate, average depth, and percent whole body movement. These parameters are continuously monitored and compared to previously measured data, control fish data, or both to determine the present physiological stress level of the exposure fish 64.

In addition, data analyzed and monitored by the water quality sensor 22 may be compared and correlated with the measured physiological responses of the aquatic organism 64 A regression analysis, for example, may be performed by the controller 32 to adjust the measured ventilatory parameters for changes in dissolved oxygen level and temperature as described in detail below. Water characteristic data from water quality sensor 22 also may be used to corroborate the ventilatory parameter analysis by controller 32. A marked change in pH level, for example, may strengthen a determination of elevated physiological stress evidenced by a change in ventilatory rate. On the other hand, further evaluation is indicated where modest changes in ventilatory behavior are detected in the absence of any measurable change in dissolved oxygen level, temperature, pH, and conductivity of the sample water stream. Data collected by the water quality sensor 22, and other system 10 components may be displayed on a digital output 89.

An optional remote monitor (not shown) provides a display of the signals as processed by the controller 32 for viewing at another location, such as an effluent treatment facility upstream of the water source being tested. Optional remote host (not shown) provides the ability to change the parameters and functions of the controller 32 in addition to monitoring and recording signals from the controller 32. The remote host also may be used to perform programmable response functions to take remedial action in response to the information provided by automated biomonitoring system 10. The remote host may be used, for example, to control an effluent water treatment process. Control of the water treatment process can thus include aquatic organism physiological stress data along with other parameters, providing real-time information on measurable biological and ecological effects of the particular water being discharged. The controller 32 may also provide a control signal via a termination panel in response to an out-of-limit condition. This control signal can be used to sound an alarm or to divert effluent water to a holding tank, for example, without the use of another microprocessor or control system.

Once the source water has been analyzed within the exposure chamber 62, the water is drained by gravity back into the reservoir 16 completing the circulation. An exposure chamber overflow drain pan 91 is located below the exposure chamber 62. The drain pan 91 catches any water that may be leaking from the pipes or from other areas within the system 10 and directs the water back into the reservoir 16. The water in the reservoir 16 may then be recirculated for further testing by being pumped from the reservoir via pump 24 through the water sensor 22 and into the exposure chamber 62 as described above. The water recirculating feature of the present invention provides several advantages over the prior art. This feature maintains a stable environment within the exposure chamber 62 for the aquatic organisms 64 being monitored. Recirculating the water provides a sufficient flow of water to the exposure chamber 62 when the source water flow is interrupted or stopped. In addition, the recirculation mode allows the testing of grab samples, as well as the static injection of toxins to water in the system and the analysis thereof.

Instead of being recirculated, the water in the system 10 may be pumped out of the reservoir 16 through a source water outlet 92 where it exits the system.

Figures 8A, 8B:
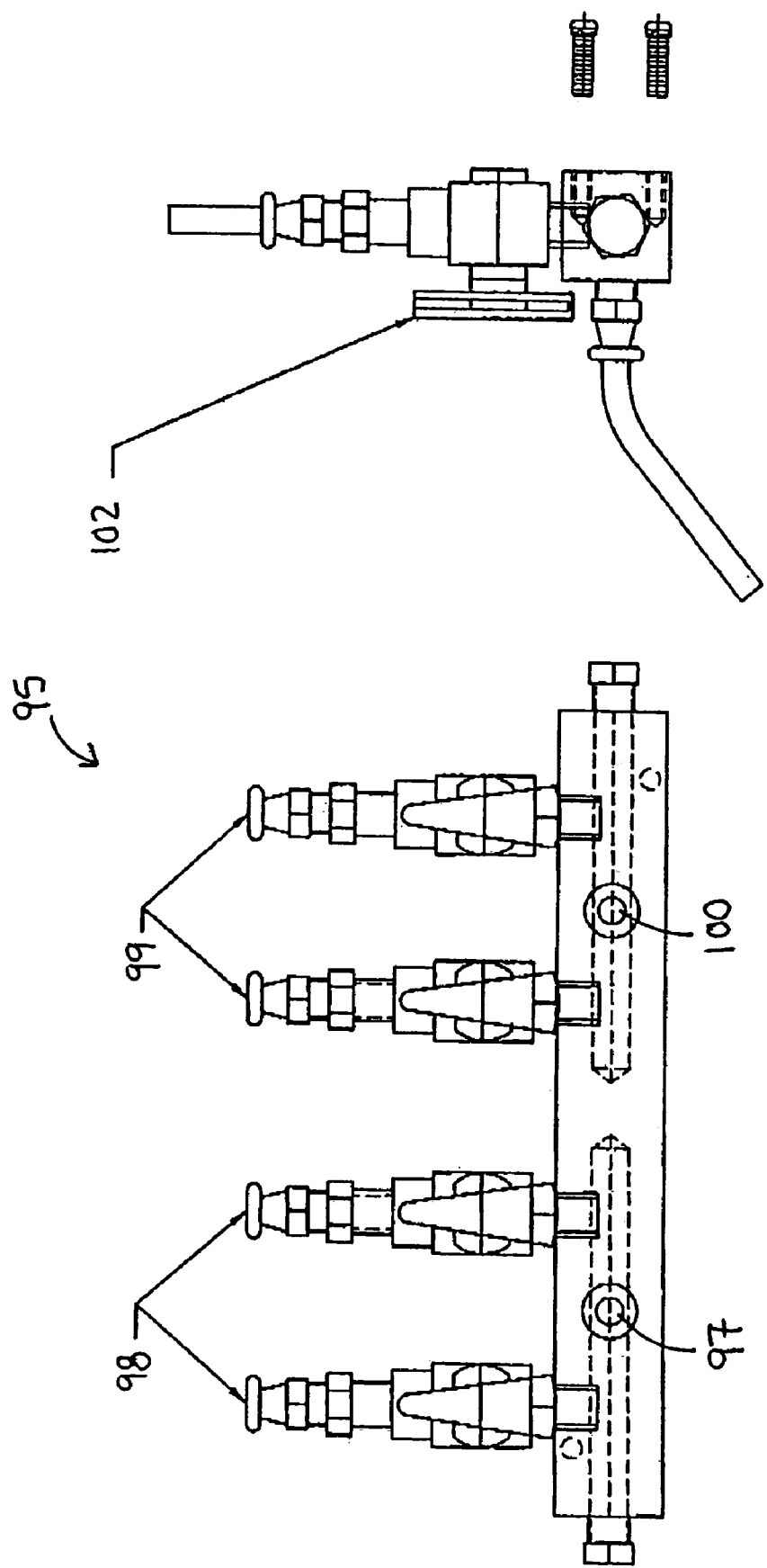
FIG. 8A is a perspective view of a heat exchange manifold assembly of a biomonitoring system made in accordance with the present invention.
FIG. 8B is a side view of a shutoff valve of a heat exchange manifold assembly.

The system 10 of the present invention may also include a heater/chiller unit for controlling the temperature of the water being analyzed. By controlling the temperature of the water within the exposure chamber 62, a stable environment is provided for the aquatic organisms 64 being analyzed. Accordingly, the integrity of the ventilatory and body movement signals being collected from the organisms 64 is maintained. As illustrated in FIGS. 1 and 7, the heater/chiller unit preferably includes a coil 93 located within the reservoir 16. A heat exchange apparatus 94 communicates with and controls the temperature of the coil 93 thereby controlling the temperature of the water within the reservoir 16. The heat exchange apparatus 94 supplies coolant to the coil 93 via a heat exchange manifold assembly 95 shown in FIGS. 1, 8A and 8B. Coolant is delivered to the manifold assembly 95 through a supply conduit 96 and enters the manifold through a manifold inlet 97. The coolant Then passes out of the manifold via a heater/chiller supply port 98, through a conduit (not shown) and into the coil 93. After flowing through the coil 93, the coolant passes through another conduit (not shown) and back into the manifold 95 via a heater/chiller return port 99. The coolant then flows out of the manifold assembly via a heater/chiller return port 100, through a return conduit 101 and back into the heat exchange apparatus 94. A shutoff valve 102 controls the flow of coolant through the supply conduit 96. The coil 93 in each reservoir 16 may be associated with a separate heat exchange apparatus 94, or a single heat exchange apparatus 94 may control the temperature of each coil in the reservoirs 16. Any heat exchange apparatus known to those having skill in the art may be used in the system 10 of the present invention. For example, the heat exchange apparatus 94 may be an ElectraCOOL L-A400 thermoelectric chiller from Advanced Thermoelectric (Nashua, N.H.).

Figure 9:
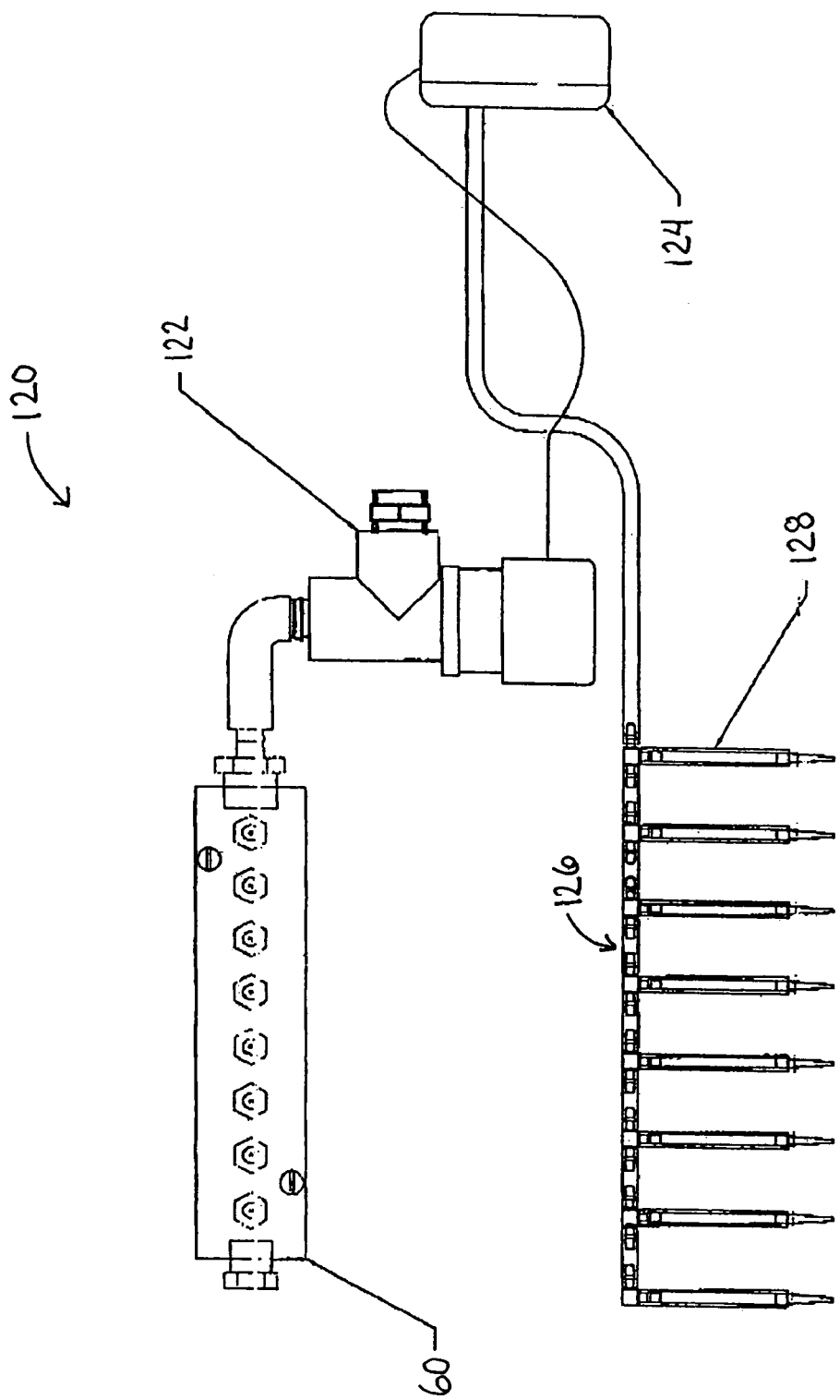
FIG. 9 is a perspective view of a backup aeration system of a biomonitoring system made in accordance with the present invention.

In the case of water flow loss in the system 10 or electrical failure within the system, a backup aeration device 120 is activated to prevent suffocation of the aquatic organisms 64. As shown in FIG. 9, the backup aeration device 120 preferably includes a pressure sensor 122 to monitor the water pressure within the conduit 123 entering the water distribution manifold 60. The pressure sensor 122 is connected to a DC powered air pump 124. The air pump 124 is activated when the water pressure within the conduit 123 falls below a predetermined level. Upon activation the air pump 124 pumps air into the water thereby supplying oxygen to the water before it enters the exposure chamber. Any air pump known to those having skill in the art may be used in the present invention. Preferably, the air pump 124 is a Bubbles of Life Series 2 power failure system. The air may be delivered to the water via an aeration manifold 126. In this embodiment air is pumped into the aeration manifold 126 and is then delivered into each exposure chamber 62 via a separate aeration manifold conduit 128. In a preferred embodiment, the air is pumped into an aeration tube which is then split into a plurality of conduits wherein each conduit delivers air to a separate exposure chamber compartment 66.

The components of the system 10 described above may be located within a single housing. However, in a preferred embodiment the first housing 11 contains the source water inlet 13, inlet conduit 14, reservoir 16, overflow pan 20, overflow drain 21, pump 24, at least a portion of sensor inlet conduit 28, source water outlet 92, outlet port 130, backup aeration device 120, water distribution manifold 60 and exposure chamber 62, and the second housing 12 contains the amplifier 69 and digital output 89. As described above, the water quality sensor 22 is preferably attached to the exterior of the housings 11 and 12.

Having provided a general description of the portable automated biomonitoring system 10, attention is now turned to a general description of its operation.

In this application, the physiological stress to bluegills (*Lepomis macrochirus*), characterized by changes in fish ventilation and movement patterns, is used as an early warning to identify developing acute toxicity of a treated groundwater discharge or effluent from a wastewater treatment facility.

A wide variety of other test organisms 64 are also available for use with the present invention, including but not being limited to rainbow trout (*Oncorhynchus mykiss*); pink salmon (*Oncorhynchus gorbuscha*); crayfish (*Orconectes* sp.); minnow and carps (Cyprinidee); bullhead and catfish (Ictaluridae); sunfish (Centrarchidas); trout, salmon and whitefish (Salmonidae); crayfish; and aquatic insects and any other species appropriate for examining water pollutant effects. Any aquatic organism that can be placed in the exposure chamber 62 and provide an electrical signal may be used in the present invention. Juvenile bluegill are often the preferred choice as the species are widely available, are easily maintained over a wide range of temperature and pH levels, are relatively sensitive to a number of pollutants, and have large opercular flaps which elicit a strong ventilatory signal. Regardless of the choice of test organism, it is desirable to acclimate the organism to the experimental conditions prior to exposure and data collection.

A typical operation begins with a plurality of fish, such as eight fish, held in control water for a three-day acclimation period followed by four days of baseline data collection. This may be performed using an exposure chamber 62, comprising eight chamber compartments 66 with each compartment housing a fish 64. The group of fish is then exposed to effluent water. In the subsequent monitoring of the effluent water, system 10 provides immediate analysis of statistically significant departures from baseline conditions for the fish exposed to the control and effluent water. After a suitable period of exposure to effluent (such as two weeks), new fish 64 are placed on-line to continue monitoring of the effluent. As a general procedure, fish feeding during testing should be avoided as feeding activity causes interference with ventilatory signal analysis.

When the system 10 identifies a potentially toxic effluent as described fully below, a water sample may be automatically collected using a sampler (not shown) for off-line chemical analysis. The water may exit the system 10 via an outlet port 130 and travel to the sampler. The remote monitor, which may be located in the treatment facility or factory control room, provides an early warning that the discharge water is inducing physiological stress to aquatic organisms 64 and, if continued, may produce harmful effects to the environment and possible danger to human health. By providing an early warning to facility operators, remedial action can be taken quickly to avoid harmful effects. As desired by the user of system 10, the toxic effluent may be automatically diverted by a control signal to storage tanks until the cause of the toxic effluent is isolated and corrected. Corrective action may, for example, require plant operators to adjust certain parameters used in the treatment of the plant water before releasing it into the discharge stream monitored by system 10. For example, corrective action may call for increasing the duration that the plant water is held in treatment tanks, reactors, neutralizing beds, and the like before allowing the water to be discharged to the environment.

In the above example, system 10 was used as an automated early warning system to identify developing acute toxicity of a treated groundwater discharge from a wastewater treatment facility. The system 10 also may be integrated with other sources of discharge water, such as a sewer treatment plant, an industrial plant, or factory for providing the same type of automated early warning and corrective action as described above. The present invention also may be used to monitor a body of water, such as a lake, bay, river, or stream, including a source of drinking water, for changes in water quality. When used to monitor the inlet to a potable water treatment facility, for example, system 10 provides an automated early warning of an inadvertent or intentional contamination of the potable water supply that may otherwise go unnoticed until human health effects are detected and traced to the source of contaminated drinking water. This application would use the same basic acclimation, baseline, and monitoring procedures as described in the above example with the same basic system components. An alarm signal in response to an identification of contaminated water by controller 32, can be provided to the appropriate health officials upon immediate detection of a possible danger.

Having provided a general description of components and operation of the present invention, attention is now turned to a detailed description of the signal processing steps performed by the system 10 to measure and analyze aquatic organism response. As mentioned above, the key physiological stress indicators used in the present invention are ventilatory rate, cough rate, average depth, and percent whole body movement. The following discussion defines the terms and mathematical operations used in this analysis.

Figure 10:
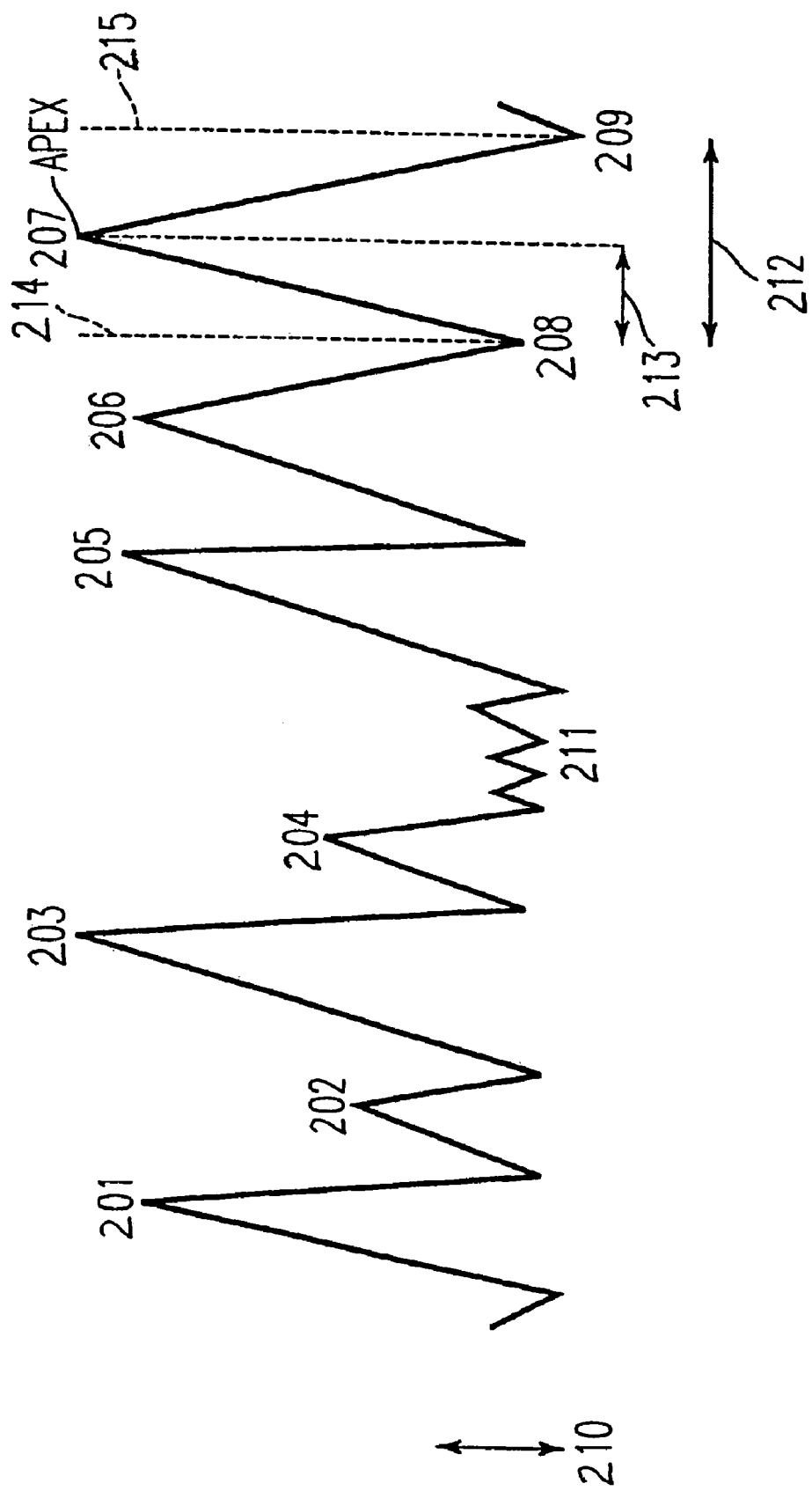
FIG. 10 is a representative signal sample illustrating ventilatory signal analysis in accordance with the present invention.

Turning to FIGS. 10 and 11, a representative signal sample and flowchart are illustrated to describe the ventilatory signal analysis performed by controller 32 in accordance with the present invention. In the following example, a twelve-bit analog-to-digital converter is used to convert the analog minus-ten to plus-ten volt signal from amplifier 46 to a digital 0 to 4095 integer value. The number of bits, analog scale, and digital scale used, however, may be varied as desired while still performing the following analysis in accordance with the present invention.

As illustrated in FIG. 10, a ventilatory signal includes a series of peaks 201–207 and troughs 208–209. Time is illustrated from left to right, with the most recent signal appearing on the far right of FIG. 10 near trough 209. Peak parameters used in this level one analysis include total duration, rear duration, peak-to-peak duration, apex, rear height, minimum height, and maximum height. A peak is defined as a signal maximum point (apex) where the difference between the value of the signal at the peak and the value of the signal at the immediately preceding or following trough is greater than a specified threshold 210. Step S301 in FIG. 11A begins signal monitoring for the next peak. The peak picking threshold 210 is generally never less than ten as measured on the 0 to 4095 integer scale, but may be adjusted upward based upon the mean maximum peak height x_bar for the previous print interval as described below. Step S302 determines whether the maximum height is greater than or equal to ten, and step S304 determines whether the same value is greater than or equal to ten percent of x_bar. If both conditions S302 and S304 are met, then the value is identified as a peak. If either one of these conditions is not met, or if both conditions are not met, then monitoring for the next peak is continued in step S303. In this way, low amplitude signals 211, which do not exceed the minimum threshold 210 are not labeled as peaks.

The mean maximum height used in step S304 is based upon data obtained in the previous print interval. A print interval is defined as a specified number of contiguous sample blocks that are analyzed and presented together in the present invention, while a sample block is defined as the ventilatory signal versus time, as illustrated in FIG. 10, over a specified duration. The print interval is normally set to fifteen minutes with sample block duration of fifteen seconds, but other values may be selected based upon user preference. The mean maximum height for the sample block is used in some cases, while the mean maximum height for the print interval is used in others. The following discussion specifies which value of x_bar is being used for a particular step in the process of FIG. 11.

Returning to FIG. 10, troughs such as 208 and 209 are defined as a signal minimum point between peaks. Total duration 212 is the time between consecutive troughs, whereas rear duration 213 is the time between a peak and the preceding trough. Rear height 214 is the difference in the absolute value of amplitude between peak value and the preceding trough value. Forward height 215 is the difference between peak value and the succeeding trough value. The minimum peak height is defined as the lesser of the rear height and forward height values, while the maximum peak height is defined as the greater of the two values.

Step S305 determines if the number of peaks in a sample block is greater than a specified whole body movement threshold, generally taken as forty-eight peaks. Again, another value may be selected for the whole body movement threshold based upon user preference. If the condition of step S305 is true, then step S306 classifies the entire sample block as whole body movement as opposed to ventilatory behavior. If the number of peaks in a sample block is less than the whole body movement threshold, then processing continues in step S307. At this point of signal analysis, the ventilatory frequency could be calculated as the number of opercular peaks thus identified in steps S304 and S305 divided by the print interval time in minutes. The present invention, however, goes beyond this first level analysis to analyze for high frequency coughs and spike coughs. As discussed in the steps below, the signal is smoothed after identifying high frequency coughs and before determining ventilatory frequency. This provides for improved data analysis in determining ventilatory parameters. In addition, the locations of the high frequency cough peaks are tagged so as not to double count these HFC-identified peaks as spike coughs.

Step S307 identifies high frequency coughs in a level two analysis as follows. If either the total duration or the peak-to-peak duration is less than the high frequency cough duration limit, then the peak is identified as a high frequency cough provided that the peaks in a peak-to-peak evaluation or the troughs in a trough-to-trough evaluation are outside of the noise band limits. Step 307 then determines whether the number of high frequency coughs is greater than or equal to the threshold for whole body movement. If so, the entire sample block is considered whole body movement as opposed to high frequency coughs or other ventilatory behavior. A time of 0.193 seconds has been used as the high frequency cough duration limit in step S307. Integer values 2108 for peaks and 1988 for troughs have been used as the initial noise band limits. After the first print interval, the mean maximum height for the print interval x_bar is calculated, and the noise band is adjusted by setting the upper limit equal to the corresponding integer equivalent of x_bar multiplied by 0.15, and the lower limit equal to the corresponding integer equivalent of x_bar multiplied by –0.15. These new noise limits are used in subsequent step S307 analyses for high frequency coughs. Again, the initial and adjusted noise level bands may be specified differently based upon user preference.

Step S308 smoothes the signal sample to remove the high frequency coughs from the data for subsequent analysis, and tags the locations of the high frequency cough peaks so as not to double count these HFC-peaks as spike coughs. The smoothing function is performed using a standard curve-smoothing algorithm, such as a low-pass digital filter, while the tagging is performed with a simple binary array of true-false data. The algorithm selected for the smoothing function should remove the high frequency coughs while preserving the remaining ventilatory data for further analysis. Step S308 provides improved data analysis in steps S309–S311 by removing the high frequency coughs from the sample data having been already analyzed for high frequency coughs in step S307. The resulting data are more amenable to opercular movement analysis and spike cough determination with the HFC peaks removed.

Step S309 performs an opercular movement analysis as follows. The ratio of the standard deviation of all maximum heights to mean maximum height of the sample block x_bar is calculated and compared with the opercular peak threshold, which is generally taken as 0.15. If less than the threshold, then all non-HFC peaks in the sample block are considered opercular movements. If the ratio is greater than or equal to the threshold, then the number of peaks with a total duration less than the whole body movement limit of 0.36 seconds is determined. If this number of peaks is greater than the whole body movement threshold of six peaks, then the sample block is considered whole body movement. If not, then the number of peaks with a maximum height greater than or equal to fifty percent of the sample block mean maximum height x_bar is the number of opercular movements. Once again, other values for peak threshold, whole body duration, and the like may be specified for use in step S309 depending on user preference.

Step S310 performs a spike cough analysis on the non-HFC peaks as follows. A given peak is considered a spike cough when the following four conditions are met. First, the number of opercular peaks in the sample block is greater than or equal to the spike cough threshold, which is generally taken as seven peaks. Second, the peak value is greater than 1.3 times the mean maximum height x_bar for the sample block. Third, the peak value is greater than 1.3 times the previous peak. Fourth, the peak value is greater than 1.25 times the first or second following peak. Again, these threshold factors may be altered from the above values depending on user preference.

Having performed the higher level analysis of steps S307–S310, ventilatory parameters are then calculated as follows. Step S311 calculates the ventilatory rate, cough rate, average depth, and percent whole body movement. Ventilatory rate (VR) is calculated in step S311 as the number of opercular peaks during a given print interval, divided by the time in minutes of the print interval. Cough rate (CR) is calculated as the sum of the high frequency coughs and spike coughs divided by the print interval time in minutes. Average depth (AD) is calculated as the mean maximum height of all opercular movement peaks during a print interval. This is the same value as mean maximum height of the print interval x_bar used in the above analysis. Percent whole body movement (PM) is the number of sample blocks in the print interval less the number of non-opercular movement blocks in the print interval divided by the total number of sample blocks in the print interval. This value may be multiplied by 100 and expressed as a percentage. Step S312 records the values of VR, CR, AD, and PM, as calculated in step S311 for subsequent use, while step S313 continues monitoring of the ventilatory signal.

Turning to FIG. 11B, further signal processing steps and functions performed by system 10 are illustrated. Step S314 calculates baseline statistics for use in determining when an out-of-control situation has occurred and when an alarm response is to be initiated by the system. The mean value and standard deviation for each of the parameters VR, CR, and AD, are calculated and stored in this step, and a Chi-square analysis is performed on percent whole body movement. An optional regression adjustment as described below may be performed in step S314 as well to adjust ventilatory parameters for changes in dissolve oxygen level and water temperature.

Step S314 may be performed over an extended period of time in which the fish 64 are exposed only to control water in the absence of any contaminants or impurities that may be present in the source water to be monitored. In this way, fish behavior may be characterized under "clean water" conditions for use in subsequent comparisons with the behavior of the same fish under exposure conditions. Step S314 also may be used to calculate moving averages for VR, CR, and AD. These data can be used to characterize changes in ventilatory behavior for either exposure or control fish, or both, over time.

Whole body movement (PM) is handled differently than the ventilatory parameters VR, CR, and AD as follows. When the level of whole body movement PM is greater than or equal to a value of twenty for at least fifty percent of the print interval, the corresponding fish is removed from the system and the data from that particular fish are not used in determining baseline statistics. The reason for this action is that significant amounts of ventilatory data are lost when whole body movement is so extensive, which could result in poor ventilatory parameter determination if the limited data were used in the subsequent analysis.

Step S314 also performs an optional regression adjustment on environmental variables as follows. Let Ti, Di denote the water temperature and dissolved oxygen levels respectively, at time i during the baseline study. Let Tm, Dm denote the baseline average levels of these variables. If the regression option is exercised, the regression model:

$$Xi = B0 + B1 Ti + B2 Di \text{ for } i=1, 2, \ldots N$$

is fitted by ordinary least squares where B0, B1, and B2 are the estimated regression coefficients used to adjust the test period responses to the levels Tm, Dm; and Xi is the measured ventilatory parameter at time i with corresponding water temperature Ti and dissolve oxygen level Di. The resulting regression coefficients are useful in applications of system 10 where there are significant changes in the dissolve oxygen level or temperature of the water being monitored. The same regression adjustment as illustrated here could be performed using other environmental variables such as pH and conductivity.

Step S315 performs signal monitoring and processing as described in steps S301–S313 of FIG. 11A, in which ventilatory parameters are characterized and quantified. Step S316 determines when an individual fish is out-of-control or beyond a predetermined threshold behavioral limit. If either VR or AD or CR is outside of a specified number of standard deviations from the baseline data provided by step S314, then the fish behavior is classified as out-of-control. The threshold used in step S316 may be determined based upon real-time control fish behavior as well as baseline statistics. In this way, the ventilatory parameters can be compared with either previously collected data from the baseline study of the same fish that are now exposed to the water being monitored, or with simultaneous data from control fish that are not exposed to the sample water source, or both baseline data and control fish data.

Step S317 determines whether there is a group response. If the number of fish characterized as out-of-control in step S316 is greater than or equal to a specified threshold, then a group response is identified and processing continues to step S319. If not, then monitoring is continued in step S318. The fish out-of-control threshold used in step S317, like the number of standard deviations used in step S314, will vary according to user preference as to the level of sensitivity desired for a particular application of the invention. A threshold of five standard deviations and seventy percent of the fish out-of-control have been used with successful results at the groundwater discharge treatment facility application described above. Specific values for a given application, however, may be selected after observing fish behavior during acclimation and baseline studies. Appropriate values will vary with local water conditions, the sensitivity of the organisms used for biomonitoring, and the desired sensitivity of the system. For example, where system 10 is used to monitor the status of a normally pristine water source, the desired sensitivity to changes in fish ventilatory parameters would be high. One may, under such circumstances, select a threshold of one standard deviation from the mean ventilatory parameters and a fish out-of-control setting of twenty-five percent as the desired thresholds used for this particular application of system 10. If two out of eight fish, for example, are out-of-control, the system 10 would initiated an alarm response.

In step S319 a group response has been identified and an alarm response, step S320, is initiated. Step S320 may be a simple audible or visual alarm or a more elaborate automated response function. For example, step S320 can be used to warn personnel at a treatment facility or factory from which the sample water is drawn of a possible problem in water quality. Also, the discharge of water can be stopped or diverted into holding tanks automatically by step S320 in reply to a group response determination in step S319 until further analysis, corrective action, or both are taken.

Step S321 determines if control fish are out-of-control using the same criteria as used in steps S316–S317 for exposure fish. If these control fish also indicate a group response, monitoring is continued in step S322. Step S323 takes and stores a water sample from the same water source as that which caused the group response. This step also can be used to initiate further remedial action not taken in step S320. Step S324 then continues monitoring of fish ventilatory behavior.

Having provided a detailed description of the signal processing performed by the present invention, attention is now turned to the various hardware components.

The process of steps S301 through S324 described above may be performed on various types of controllers 32. The preferred embodiment uses a standard personal computer (microprocessor) to perform this function for ease of programming, versatility, and overall friendly user interface. For example, the user selected parameters discussed above (group response threshold, whole body movement threshold, sample interval duration, and the like) are conveniently presented in a screen menu with a standard PC, the operation of which is generally well known without special training in how to use the controller 32. In this particular embodiment, a 120 MHZ personal computer with 16 MB of RAM is used for both the controller 32 and the remote host. The interface between the controller 32 and the other system components is described below with reference to FIG. 12.

Amplifier 69 may be any device capable of amplifying the signals from electrodes 67 and 68. In the present embodiment it is a multiple channel amplifier with a low-pass analog filter. It receives the raw input signals from electrodes 67 and 68 of exposure chamber 62, amplifies the signals, filters out high frequency signals beyond a certain frequency, then transmits the filtered and amplified analog signals to a controller 32 via signal cables 90. In this particular embodiment, a 32-channel, rack mounted amplifier system from Dataforth, Inc. was selected for this function. It provides amplification by a factor of 1000, and filters out high frequency signals beyond 50 Hz so as to remove noise produced by the 60 Hz power supply. The commercially available amplifier 69 was modified with the addition of two 470-microfarad electrolytic capacitors to the front end of the amplifier system to eliminate D.C. offset created by exposure chamber 62.

As illustrated in the previous discussion, portable system 10 provides a general-purpose automated biomonitoring system for use in monitoring the water quality of any source of water, and is readily integrated with other control systems or data monitoring devices.

Turning to FIG. 12, a schematic of an internal carrier board 400 is illustrated for integrating the present invention with a standard PC as controller 32. Carrier board 400 is a data acquisition board that interfaces directly with the internal bus of ISA and EISA computers, and may be plugged directly into a PC motherboard to provide integration of controller 32 with other components of system 10. Carrier board 400 includes expander/sequencer module 402, output module 403, and input module 404.

The ventilatory signals from amplifier 69 are provided as analog input data to module 402 via signal cables 90. These analog ventilatory signals are provided to input module 404 via a daisy chain (internal bus) between modules 402 and 404. Input module 404 receives analog ventilatory signals from module 402, amplifies the signals by a factor of ten and performs an analog-to-digital conversion of the data signals, which are then read by controller 32 and analyzed as described above. These ventilatory data signals also are written by controller 32 to output module 403, which performs a digital-to-analog conversion, and transmits the resulting ventilatory signals to termination panel 140 via cable 414. The termination panel 140 can be used to provide control signals to components such as a solenoid valve 144 and the sampler 146. The analog ventilatory data signals at terminal panel 140 may be viewed on oscilloscope 142, which is connected to termination panel 140 via cable 416.

Module 404 may also receive analog input signals from termination panel 140 via cable 412. This feature is used to provide controller 32 with information from an external source such as a water treatment facility. For example, when the facility is discharging effluent water, a signal may be sent from the treatment facility control room to system 10 indicating that a discharge has occurred. This information would be provided to controller 32 via termination panel 140, cable 412, and input module 404. The analog signals received by input module 404 are converted to digital form and transferred to controller 32.

Internal carrier 400 further includes a digital output port 405 to send digital control signals to termination panel 140 via cable 417. Digital output port 405 is used in this example embodiment to control solenoid valve 144, water sampler 146, and control signal 148 as described with reference to FIG. 13 below.

The internal carrier board 400 may itself be, or may be assembled from, off-the-self components. In this particular embodiment, internal carrier board 400 is a model PCI-20041C-2A. Module 402 is an analog expander/sequencer option module, model PCI-20031M-1. Output module 403 is a 12-bit analog output module, model PCI- 20003M-2. And input module 404 is a 12-bit analog input module, model PCI-20002M-1, all of which are commercially available from Intelligent Instrumentation, Inc.

Turning to FIG. 13, a schematic of a termination panel 140 is illustrated. Termination panel 140 includes signal module 410 and control module 420. Signal module 410 receives analog input from module 403 of internal carrier 400 via cable 414. Module 410 includes analog input terminal strip 413 and analog output terminal strip 415. Channel 0 and 1 of output terminal 415 are used in this illustration to provide an analog voltage signal to oscilloscope 142 via cable 416. Channel 0 of input terminal 413 receives signal 418 from an external source indicating, for example, that a wastewater or effluent discharge is taking place. Additional terminals for further input data and output functions are provided for expansion as may be desired for a particular application of the invention. More information from a water treatment facility, for example, may be provided and analyzed by controller 32 via the unused channels available on input terminal 413. Similarly, additional output information could be provided to remote sites, monitoring stations, and the like using the unused channels of output terminal 415.

The function of terminal panel 140 may be divided among a number of separate devices, perhaps even eliminating the need for this particular component of system 10. It is used in this embodiment to separate power supply 422 and other component wiring from controller 32 and amplifier 69, thus avoiding possible signal noise that could result from a clustering of components.

Termination panel 140 also includes control module 420 for controlling certain component functions based upon a digital signal from controller 32. Control signals are received from controller 32 via digital output module 405 and cable 417. A 120-volt AC power supply 422 is provided to module 420 for use in opening or closing water control valves, sounding alarms, and similar functions. In this embodiment, module 420 provides output control of solenoid valve 144, water sampler 146, and control signal 148. Solenoid valve controller 144, in response to a signal from controller 10 via termination panel 140, provides water to sensor 22 for sensing water characteristics from either source via stream or control water source. In this way, sensor 22 can be calibrated automatically by controller 32 using the known water characteristics of control water source. Sensor 22 is a commercially available water quality analyzer such as the $H_2O$ multiprobe available from by Hydrolab, Inc.

Control signal 148 may be used to energize a simple audible alarm and lamp to warn of a water quality problem, or it may be a previously established response procedure to automatically isolate or correct the cause of the problem. The latter is accomplished for a given application of the invention with the assistance of local facility engineers using standard equipment and procedures. For example, corrective action at a particular water treatment facility may call for additional holding time in a reaction vessel, aeration pond, or the like before the water is discharged to the environment. In the case where system 10 is used to monitor a source of drinking water before it enters a potable water system, automated corrective action may call for immediate isolation of water source to prevent it from entering the potable water system until the water quality problem has been resolved. As illustrated in the above discussion, system 10 provides a general-purpose portable automated biomonitoring system for use in monitoring the water quality of any source of water, and is readily integrated with other control systems or data monitoring devices.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

We claim:

1. A portable system for monitoring and evaluating water quality using ventilatory behavior and body movement of an aquatic organism, comprising:
    an exposure chamber for housing an aquatic organism;
    a water inlet for directing water to the exposure chamber;
    an electrode for sensing and quantifying ventilatory behavior and body movement of said aquatic organism into data and outputting said data as a behavioral signal;
    a controller for receiving the behavioral signal and determining a plurality of ventilatory parameters based on the behavioral signal;
    a recirculating apparatus for recirculating water to the exposure chamber, the recirculating apparatus comprising a water reservoir, a water quality sensor and a pump for pumping the water from the water reservoir through the water quality sensor and into the exposure chamber; and
    a first portable housing;
    wherein the exposure chamber, electrode, water reservoir and pump are disposed within the first housing.

2. The system of claim 1, wherein the water quality sensor is pivotally attached to the exterior of the first housing via a calibration bracket.

3. The system of claim 1, further comprising:
    a second portable housing in communication with the first portable housing; and
    electrical components disposed within the second housing;
    wherein the water quality sensor is pivotally attached to the exterior of the first housing and the second housing.

4. A portable system for monitoring and evaluating water quality using ventilatory behavior and body movement of an aquatic organism, comprising:
    an exposure chamber for housing an aquatic organism;
    a water inlet for directing water to the exposure chamber;
    an electrode for sensing and quantifying ventilatory behavior and body movement of said aquatic organism into data and outputting said data as a behavioral signal;
    a controller for receiving the behavioral signal and determining a plurality of ventilatory parameters based on the behavioral signal;
    a recirculating apparatus for recirculating water to the exposure chamber; and
    a heater/chiller unit for controlling a temperature of water being tested by the system.

5. The system of claim 4, wherein the recirculating apparatus comprises:
    a water reservoir;
    a water quality sensor; and
    a pump for pumping the water from the water reservoir through the water quality sensor and into the exposure chamber.

6. The system of claim 5, wherein the recirculating apparatus further comprises:
    a water distribution manifold for dividing the water before it enters the exposure chamber.

7. The system of claim 5, wherein the water quality sensor senses a characteristic of water supplied to the exposure chamber, wherein the controller is responsive to the water quality sensor by comparing the water characteristic with the corresponding behavioral signal to determine when a change in one or more of the ventilatory parameters occurred at the approximate time that a change in water characteristic occurred.

8. The system of claim 7, wherein the water characteristic includes dissolved oxygen level and temperature.

9. The system of claim 4, further comprising:
    a backup aeration device for preventing suffocation of the aquatic organism in the case of water loss from the system or electrical failure of the system.

10. The system of claim 4, wherein the controller further determines when one or more of the parameters exceed a threshold.

11. The system of claim 4, wherein the controller determines ventilatory frequency, average ventilatory depth, and cough rate of the organism based on the behavioral signal.

12. The system of claim 4, further comprising:
    a water sampler responsive to the controller for automatically sampling water supplied to the exposure chamber for subsequent analysis.

13. The system of claim 4, wherein the exposure chamber is supplied with water to be discharged into the environment, including means for directing the water into a holding tank when the controller determines that one or more of the ventilatory parameters exceed a threshold.

14. The system of claim 4, wherein the exposure chamber includes a plurality of compartments, each of which can house an aquatic organism.

15. The system of claim 4, wherein the aquatic organism is a fish.

16. A portable apparatus for generating behavioral signals of aquatic organisms indicative of water quality, comprising:
- a first portable housing including a water inlet;
- an exposure chamber disposed within said first portable housing for housing an aquatic organism, said exposure chamber having an inlet and an outlet;
- an electrode disposed within said exposure chamber for sensing and quantifying ventilatory behavior and body movement of said aquatic organism into data and outputting said data as a behavioral signal;
- an amplifier for amplifying the behavioral signal; and
- a recirculation unit that circulates water from the outlet of said exposure chamber, through a fluid flow path and to the inlet of said exposure chamber, said recirculation unit including:
  - a water reservoir in fluid communication with said exposure chamber, the water reservoir including an inlet and an outlet;
  - a water quality sensor in fluid communication with said water reservoir and said exposure chamber, said water quality sensor being pivotally mounted to said first portable housing;
  - a pump disposed between said water reservoir and said water quality sensor to assist fluid flow between from the water reservoir to the water quality sensor.

17. The system of claim 16 wherein said water reservoir and said pump are disposed within said first portable housing.

18. The system of claim 17 further comprising a second portable housing disposed contiguous to said first portable housing, said amplifier being disposed in said second portable housing.

19. The system of claim 18 further comprising a bracket mounted to said first and second portable housings, said bracket including a plate and an adjustable clamp pivotally mounted to the plate configured to hold said water quality sensor.

* * * * *